United States Patent
Yeo et al.

(10) Patent No.: US 7,450,687 B2
(45) Date of Patent: Nov. 11, 2008

(54) METHOD FOR VERIFICATION OF INTENSITY MODULATED RADIATION THERAPY

(75) Inventors: Inhwan Yeo, Voorhees, NJ (US); Brian Wang, Merchantville, NJ (US)

(73) Assignee: University of Medicine and Dentistry of New Jersey, New Brunswick, NJ (US)

( * ) Notice: Subject to any disclaimer, the term of this patent is extended or adjusted under 35 U.S.C. 154(b) by 98 days.

(21) Appl. No.: 11/529,906

(22) Filed: Sep. 29, 2006

(65) Prior Publication Data

US 2007/0071169 A1    Mar. 29, 2007

Related U.S. Application Data

(60) Provisional application No. 60/721,759, filed on Sep. 29, 2005.

(51) Int. Cl.
*A61N 5/10* (2006.01)
(52) U.S. Cl. .......................................................... 378/65
(58) Field of Classification Search .................... 378/65
See application file for complete search history.

(56) References Cited

U.S. PATENT DOCUMENTS 6,636,622 B2 * 10/2003 Mackie et al. .............. 382/132

OTHER PUBLICATIONS

J. V. Siebers, J. O. Kim, L. Ko, P. J. Keall, R. Mohan; "Monte Carlo computation of dosimetric amorphous silicon electronic portal images"; Med. Phys. 31 (7); Jul. 2004; pp. 2135-2146.
J. M. Kapatoes, G. H. Olivera, P. J. Reckwerdt, et al.; "Delivery verification in sequential and helical tomotherapy"; Phys. Med. Biol. 44; Apr. 7, 1999; pp. 1815-1841.
J. M. Kapatoes, G. H. Olivera, K. J. Ruchala, J. B. Smilowitz, P.J. Reckwerdt, T.R. Mackie; "A feasible method for clinical delivery verification and dose reconstruction in tomotherapy"; Med. Phys. 28 (4); Apr. 2001; pp. 528-542.

* cited by examiner

*Primary Examiner*—Edward J. Glick
*Assistant Examiner*—Mona M Sanei
(74) *Attorney, Agent, or Firm*—Watov & Kipnes, P.C.; Kenneth Watov

(57) ABSTRACT

An accurate method for inversely verifying a therapeutic radiation dose delivered to a patient via an x-ray delivery system without involving any computational iteration was developed. The usage of it includes detecting the transmitted radiation dose image after passage through the patient, imaging the patient during treatment to anatomically record information of the patient, followed by inversely verifying through use of both the detected radiation image and the imaging data, the actual radiation dose delivered to the patient, and comparing the level of the dose delivered to a previously planned dose to determine whether the planned dose was delivered, or whether an overdose or underdose occurred.

20 Claims, 22 Drawing Sheets
(13 of 22 Drawing Sheet(s) Filed in Color)

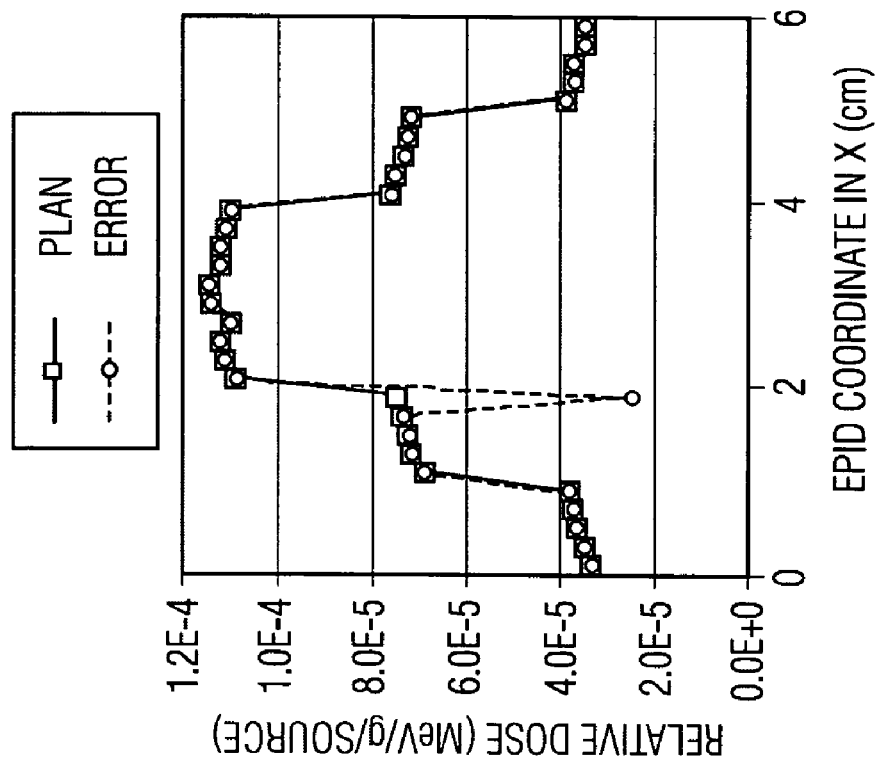
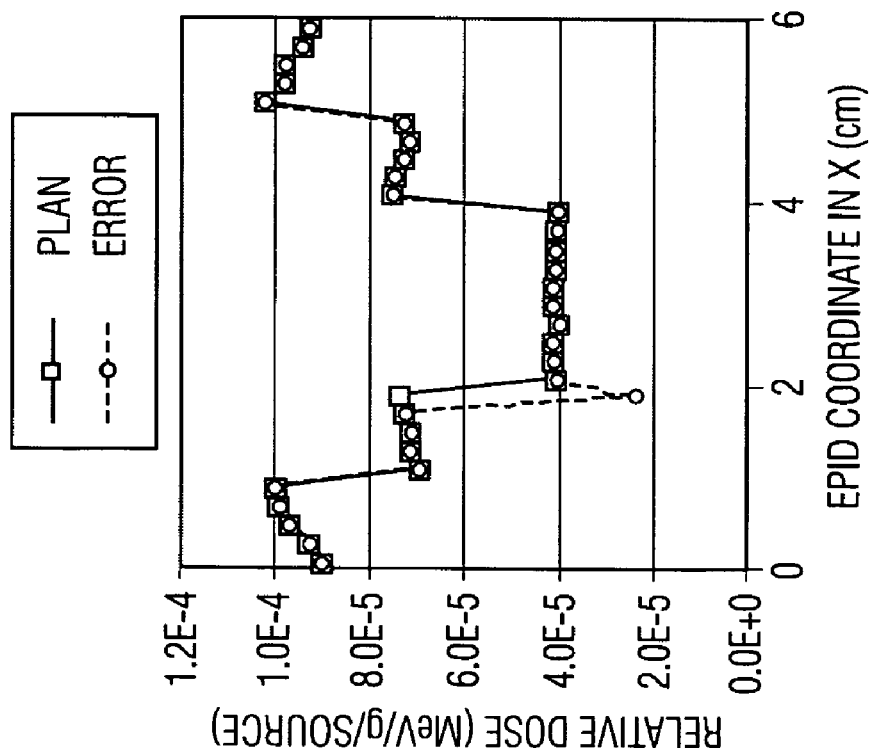
FIG. 6B
FIG. 6A

METHOD FOR VERIFICATION OF INTENSITY MODULATED RADIATION THERAPY

RELATED APPLICATION

The present Application is related to and takes priority from Provisional Application No. 60/721,759, filed on Sep. 29, 2005. The teachings of this related Provisional Application are incorporated herein to the extent that they do not conflict herewith.

FIELD OF THE INVENTION

The present invention relates generally to Intensity Modulated Radiation Therapy (IMRT), and more particularly to methods for verifying the delivery of a planned radiation dose to a patient.

BACKGROUND OF THE INVENTION

The current trend of radiation therapy is moving toward precise dose delivery, which employs an extensive degree of radiation beam intensity modulation and on-line and real-time imaging. The IMRT involves various sources of uncertainty associated with multi-leaf collimator (MLC) positional reproducibility, beam output stability, mechanical isocentricity, and insufficient beam modeling in treatment planning. As a result, the dose delivered to a patient does not accurately represent the dose distribution generated from treatment planning. Therefore, verifying the delivery of a planned radiation dose is required for successful radiation therapy. It is done mostly by comparing the dose distribution from the planning with that from the measurement of the dose delivery. The verification idealistically should be accurate, representative of actual treatment (measurement condition), demand little labor, and require short processing time. Although diverse methods of the verification exist, they can be classified whether the measurement is done before or during treatment. In the following, a brief review is provided.

A group of methods exist, which are based on measurement prior to treatment. The measurement mostly is done on a dosimeter such as x-ray film or an EPID (electronic portal image device) embedded in phantom slabs, and thus are provided with a scattering condition. As such a condition simulates in-patient environment, this group offers true dosimetric verification.

Another group of methods exist that utilizes measurement during treatment. The measurement is to detect transmitted radiation through a patient under treatment. The treatment can be verified (forward verification) in the EPID by comparing the dose image from calculation with that from measurement. Furthermore, the dose can be reconstructed (inverse verification) in a patient from dose image in the EPID, using a computational technique on patient anatomy provided by computer tomography, or CT. Therefore, this group is more representative of actual treatment than the previous group, provided that the real anatomical information of a patient under treatment can be acquired. In addition, this group contributes to adaptive radiation therapy by providing the reconstructed dose. While this group does not achieve true dosimetric verification by employing measurements in a scatter environment, it does fulfill the verification of the dose delivery. This group eliminates human efforts for measurement setup prior to treatment, which is contrary to that required for the first group. As verification involves the two components of calculation and measurement, any methods thus in their application are associated with uncertainty and inaccuracy typically involved in measurements and calculations. When it comes to calculations, the calculation methods for both groups are mostly based on moderately accurate algorithms: calculation algorithms are less accurate than the Monte Carlo (MC) radiation transport method. This in particular challenges the second group in modeling scatter behind a patient. To account for the scatter, an iterative approach, between the two calculation planes of a patient and the EPID, has been made for the dose reconstruction. For this method, convergence is not guaranteed in theory, although good agreements were shown as compared with measurements. On the contrary, in the other forward approach, the scatter could be accurately accounted for in the form of kernels calculated by the MC technique for various EPIDs.

SUMMARY OF THE INVENTION

An object of the invention is to provide an accurate method for verifying the delivery of a planned radiation dose to a patient by reconstructing delivered beam intensity and dose deposited in a patient, particularly when a complex form of radiation delivery is employed, such as Intensity Modulated Radiation Therapy (IMRT), for example.

Another object of the invention is to provide a non-iterative method of verification of a planned radiation dose.

Another object of the invention is to provide an algorithm that is designed to handle a complex beam arrangement, such as IMRT, for example, for verifying the delivery of a planned radiation dose to a patient.

Another object of the invention is to provide a method for verifying the delivery of a planned radiation dose that is within a defined spatial precision limited by the spatial resolution of EPID and constraints associated with current radiation delivery techniques.

Another object of the invention is to provide a method for verifying the delivery of a planned radiation dose, whereby the method uses a representation of the actual treatment setup by using an on-line anatomical patient under treatment, thus representing the actual patient.

Another object of the invention is to provide a method for dose reconstruction after radiation therapy on which adaptive radiation therapy is based.

The method we propose is an inverse method, and is not affected by the above drawbacks associated with inferior accuracy and iterative approach. By taking advantage of the existing superior accuracy associated with the MC method in fully modeling radiation transport through patient and the EPID and by utilizing the measured value of transmitted dose and the anatomical representation of a patient under treatment, this method in principle ensures one of the most accurate verifications and dose reconstructions for IMRT.

The present method verifies the delivery of IMRT by reconstructing the delivered intensity distribution (or map) and the radiation dose in a patient, wherein the patient in treatment condition is represented by on-board CT imager. The method is based on a computational algorithm that linearly describes a physical relationship between beam intensity and doses deposited in a patient and an electronic portal imaging device (EPID). The relationship is quantified in the form of Responses that are deposited doses in a patient and EPID per unit intensity. According to this linear relationship, the doses at a single point in the patient and EPID are equal to Responses in patient and EPID, respectively, multiplied by the corresponding intensity, and integrated over the entire intensity map. Responses can be accurately calculated using Monte Carlo (MC) particle transport techniques, wherein the MC with the most accurate models of radiation interaction in a medium traces the actual radiation transport process from the radiation emission plane to the calculation plane within a patient and the plane on EPID through the patient. Keeping an intensity map as unknowns and providing the dose on EPID with measurement, the linear relationship can be inversely and non-iteratively solved generating a unique solution of intensity map. The reconstructed intensity map now accounts for what was actually delivered to the patient. The algorithm was validated through a computational demonstration on both homogeneous and heterogeneous phantoms. For demonstration, two Responses in phantom and EPID were first calculated for each IMRT segment. Two IMRT beams of pyramid and inverse pyramid shapes were constructed by weighting each segmental intensity differently. An error was designed by reducing the intensity of a certain segment for the IMRT beams, and the radiation dose received in an EPID was calculated for such a condition. For the validation, the forward calculation previously attained was inversely reproduced. Using the calculated dose in EPID, the algorithm was solved to reconstruct the intensity map. Then, the doses in the phantoms were calculated weighting the pre-calculated Response in phantom by the reconstructed intensity map. Comparing the reconstructed intensity map with the imposed intensity map, the result showed a negligible error of a few tenths of a percent for the verification of IMRT. The error is due to rounding-off of data. The dose difference in the phantoms caused by the designed error was also obtained, showing the dosimetric effect of such an error. This validation has shown that the inventive algorithm is computationally feasible for the verification of IMRT, and useful for application in adaptive radiation therapy.

Radiation dose delivery can be verified to the spatial precision level limited by the pixel size of the EPID used, and constraints of the delivery techniques. Note that although the present invention is taught for use with an IMRT system, it is not meant to be so limited. It is believed the invention can readily be used in other therapeutic x-ray delivery systems.

BRIEF DESCRIPTION OF THE DRAWINGS

The patent or application file contains at least one drawing executed in color. Copies of this patent or patent application publication with color drawings will be provided by the Office upon request and payment of the necessary fee.

The present invention is described in detail below with reference to the drawings, in which like items are identified by the same reference designation, wherein:

FIG. 6A shows forwardly calculated doses in EPID from an inverse pyramid beam without (plan) and with a designed error.

FIG. 6B shows forwardly calculated doses in EPID from a pyramid beam without (plan) and with a designed error.

DETAILED DESCRIPTION OF THE INVENTION

Various embodiments of the present invention will now be described in detail with reference to FIGS. 1 through 21. In general terms, the method of the present invention overcomes the drawbacks in the prior art. Also, unlike the prior art, the method of the present invention provides inverse verification of a radiation delivery without using any computational iteration through use of a method that fully calculates MC (Monte Carlo) Responses in a patient, and also in an EPID. The method reconstructs an intensity map that is used to deliver a radiation beam in a patient, in addition to providing reconstruction for the dose deposited in a patient. The present method takes advantage of the high-level of accuracy associated with the MC method to fully model the radiation transport, the measured value of transmitted dose, and the anatomical representation of a patient under treatment. It is believed that the present method provides one of the most accurate IMRT verification and dose reconstruction methods available.

Figure 1:
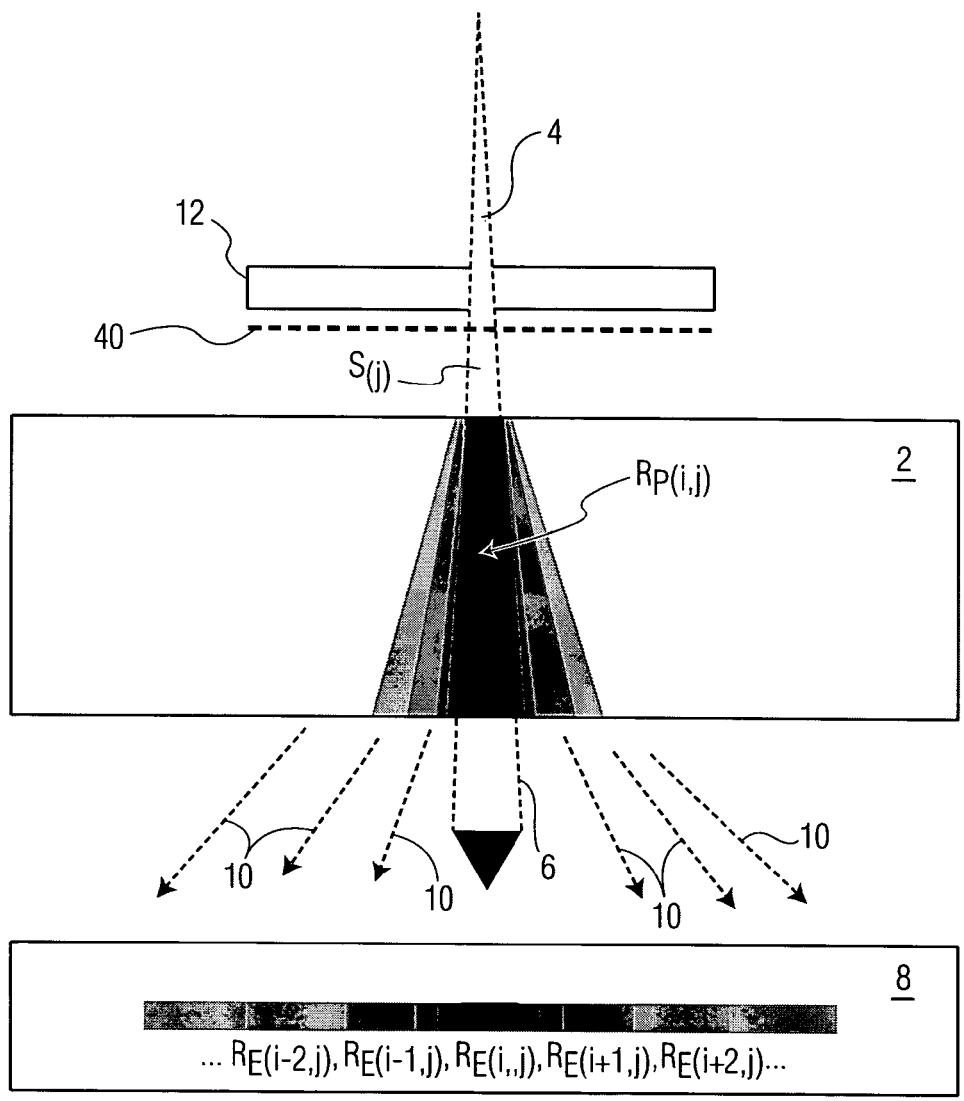
FIG. 1 is a block schematic and pictorial diagram showing the radiation dose spread from a unit beam segment for IMRT in a phantom passing through to an EPID, for an embodiment of the invention.
Figure 2:
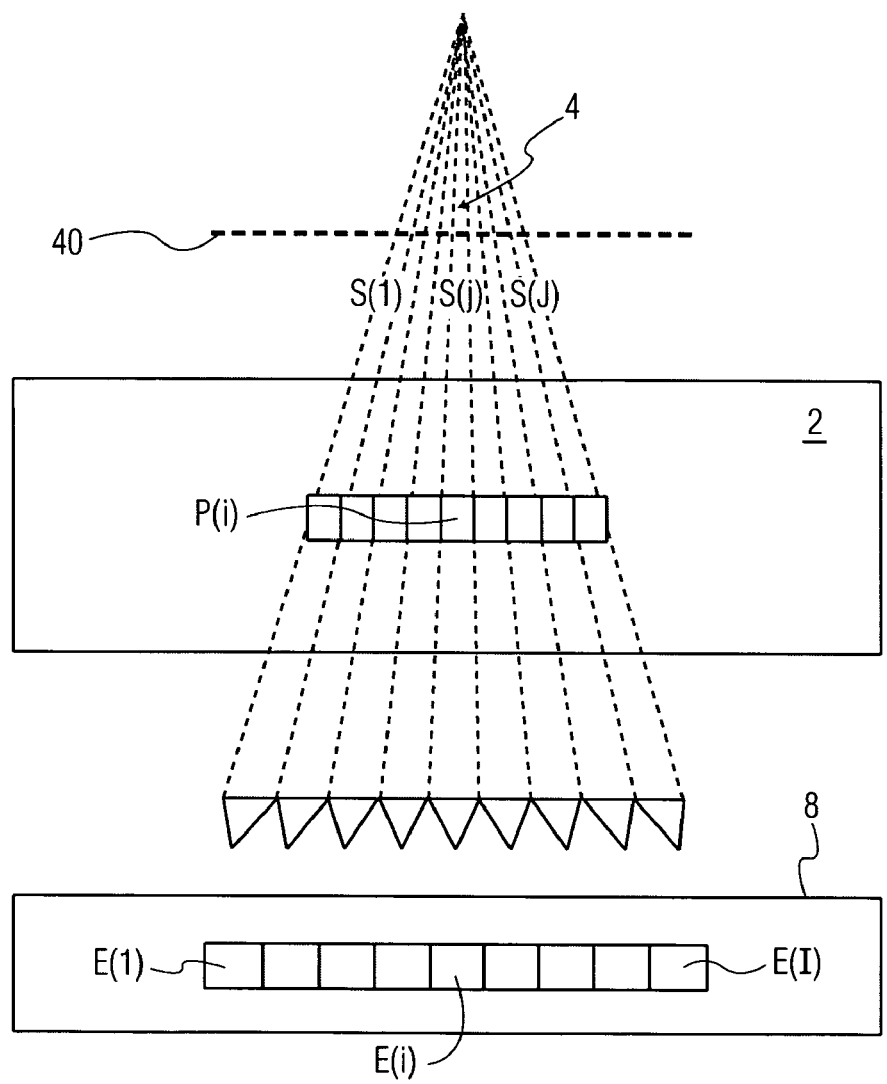
FIG. 2 is a block schematic diagram showing a computational model for the reconstruction of intensity map and dose from an EPID dose, for one example of an embodiment of the invention.

Theoretical Formulation:

The MC method, as one of the most accurate methods that describe radiation interaction with matter, can model complete radiation transport processes from a target to the measurement plane of an EPID through a patient medium. On a beam plane, a segmental beam for IMRT is characterized by its spatial position. If it is irradiated toward a particular direction (without modeling a detailed beam term for demonstration purposes), it undergoes interactions and deposits a radiation dose in a patient phantom along the track of its travel. With reference to FIG. 1, after undergoing attenuation through a phantom 2, the remaining intensity 6 of the beam 4 deposits a primary dose in a specific area in an EPID 8 (i.e. energy deposition in the phosphor plate in the EPID) that is positioned in the path of the beam 4. It also deposits a dose due to the scattered radiation 10 generated within and from a phantom 2 in all the other areas in EPID 8. The primary and scattered doses in EPID 8 are indicated by the gray scale horizontally placed in EPID. In FIG. 1, there are two special indexes in the X-direction, namely, 'i' for phantom 2 and EPID 8 dose Responses, and 'j' for position of the x-ray beam 4. Note that beam 4 is a segmental beam corresponding to a unit MLC 12 step for IMRT. Using this technique, the dose distributions across the measurement plane of EPID 8 (Beam-to-EPID Response or $R_E$) as well as that within the volume of a patient ($R_P$) can be calculated for each unit step of beam 4 on a beam plane (for example, 0.5×0.5 cm², 0.2×0.2 cm², and etc). S(j) is defined as the beam intensity or intensity at the beam position 'j'; $R_E(i,j)$ is $R_E$ at the point corresponding to index 'i' on EPID 8 from the segmental beam at the beam position 'j' on a beam plane. $R_P(i,j)$, defined as the beam-to-phantom Response, is the dose at the point corresponding to index 'i' in phantom 2 from the segmental beam irradiated at the beam 4 position 'j' on a beam plane 40. Then, the dose (or dose image if measured) at a single point on EPID 8 (E) is represented by a set of linearly independent equations (1A, 1B, and 1C) with the help of FIG. 2, as follows:

$$E(1) = R_E(1,1)S(1) + R_E(1,2)S(2) + \ldots + R(1,j)S(j) + \ldots + R_E(1,J)S(J), \quad (1A)$$

$$E(i) = R_E(i,1)S(1) + R_E(i,2)S(2) + \ldots + R_E(i,j)S(j) + \ldots + R_E(i,J)S(J), \quad (1B)$$

$$E(I) = R_E(I,1)S(1) + R_E(I,2)S(2) + \ldots + R_E(I,j)S(j) + \ldots + R_E(I,J)S(J), \quad (1C)$$

In equations 1A through 1C, E(i) is the cumulative dose on a single point on EPID 8; P(i) is the dose in a patient phantom 2, where i is 1 through I and j=1 through J and I≧J. Note that $R_P$ is defined at various rows of voxels in the two-dimensional patient phantom 2.

In matrix formation, a set of equation (1) can be written as, $$\underline{E} = \underline{\underline{R}}_E \underline{S}, \quad (2)$$

where $\underline{E}$ is the vector of E, $\underline{S}$ is the vector of S, and $\underline{\underline{R}}_E$ is the matrix of $R_E$. Then, by matrix inversion the beam intensity vector is obtained as $$\underline{S} = \underline{\underline{R}}_E^{-1} \underline{E}. \quad (3)$$

Replacing $\underline{E}$ with the corresponding measured values in EPID 8 (given that MC calculation is accurate), the beam intensity $\underline{S}$ can be inversely and non-iteratively reconstructed. In this way, what was actually delivered to a patient was accounted for and thus revealed. Then, the difference between the imposed (i.e. representing the optimized intensity from treatment planning) and reconstructed intensity $\Delta\underline{S}$ can be calculated by comparing the two for future adjustment. Therefore, radiation dose delivery such as IMRT can be verified to the spatial precision level, only limited by the voxel (or pixel) size of the EPID, constraints of delivery techniques, and computational accuracy. The difference can be alternatively calculated as follows:

$$\Delta\underline{S} = \underline{\underline{R}}_E^{-1} \Delta\underline{E}, \quad (4)$$

provided $\Delta\underline{E} = (\underline{E}^{predicted} - \underline{E}^{measured})$ where $\underline{E}^{predicted}$ is the vector for forwardly calculated dose in EPID and $\underline{E}^{measured}$ is the vector for measured dose in EPID 8 that may contain errors. For the above calculations, a unique solution exists as long as the number of unknowns (J) is smaller than or equal to that of equations (I), while the latter is equal to the number of data points in EPID 8 defined by the required spatial resolution for calculational voxels in EPID 8 and a patient 2.

In a patient, a dose vector can be expressed similarly to equation (2):

$$\underline{P} = \underline{\underline{R}}_P \underline{S}, \quad (5)$$

where $\underline{P}$ is the vector of P corresponding to the X direction (for a two-dimensional X-Z plane, the two-dimensional dose matrix $\underline{\underline{P}}$ of P applies), $\underline{\underline{R}}_P$ is the matrix of $R_P$. Note that equation (5) is a general relationship valid for any source term of beam intensity $\underline{S}$, not limited to the reconstructed one. With known matrices, $\underline{\underline{R}}_E$ and $\underline{\underline{R}}_P$ (to be calculated and predetermined), and $\underline{E}$ (to be measured), $\underline{P}$ can now be easily solved by equation (6) as follows:

$$\underline{P} = \underline{\underline{R}}_P \underline{\underline{R}}_E^{-1} \underline{E}. \quad (6)$$

For each unit step beam, the previously calculated dose Response $\underline{\underline{R}}_P$ within a patient phantom 2 can now be scaled by the reconstructed segmental-beam intensity $\underline{\underline{R}}_E^{-1} \underline{E}$ to reconstruct $\underline{P}$ without requiring the information of beam intensity as well as another series of dose calculations. In algebraic explanation similar to what equations 1A, 1B, and 1C provide for E(i)'s, the distribution for each voxel in a patient P(i) can simply be obtained by summing the distributions delivered by each unit segmental beam intensity S(j). Using the equation (6), if necessary, $\underline{P}$ can be directly calculated without explicitly calculating for $\underline{\underline{R}}_E^{-1} \underline{E}$ or $\underline{S}$. Then, the difference $\Delta\underline{P}$ between the planned (forwardly calculated using planned S) and reconstructed doses can be calculated by comparing the two for future adjustment. The difference can be alternatively calculated by equation (7) as follows:

$$\Delta\underline{P} = \underline{\underline{R}}_P \underline{\underline{R}}_E^{-1} \Delta\underline{E}, \quad (7)$$

as the data set of $\Delta\underline{E}$ is one-dimension less than that of $\Delta\underline{P}$.

Simulation on Phantom:

Forward Calculation:

This method was validated through the following simulation. The simulation geometry includes a beam term 40, a homogeneous phantom 2, and an EPID 8 (FIG. 1). The dose Responses on the EPID $\underline{\underline{R}}_E$ and in a phantom $\underline{\underline{R}}_P$ on a mid plane were calculated for thirty spatial beam segments 4(index 'j') each with the size of 0.2×40 cm². Each segment is emitted with a distribution of directions following the fan lines from a target. These segments altogether correspond to the field width of 6 cm, in this example, a size suitable for prostate. The segments were individually irradiated on the flat phantom. The two-millimeter resolution was chosen because it is a relatively fine resolution and it corresponds to a tolerance for the reproducibility of field sizes by the AAPM (American Association of Physicists in Medicine) 40 report. No spatial segmentation in the Y direction was modeled. Thus, the Responses were calculated per unit intensity in terms of particle number for each segment; scoring voxel (volume element) dimensions were 0.3×45×0.2 cm³ and 0.2× 30×0.2 cm³ for the two Responses, respectively, for example. An x-ray beam of a single energy of 2 MV was used. Simplified but suitable models for demonstration purposes have been employed.

Figure 3A:
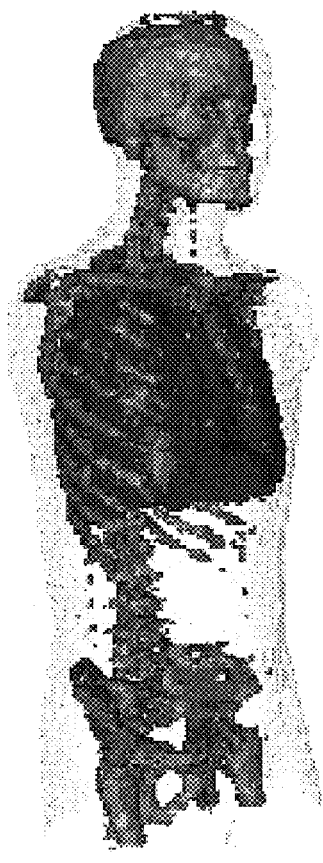
FIG. 3A shows a 3D image of a Rando® phantom.
Figure 3B:
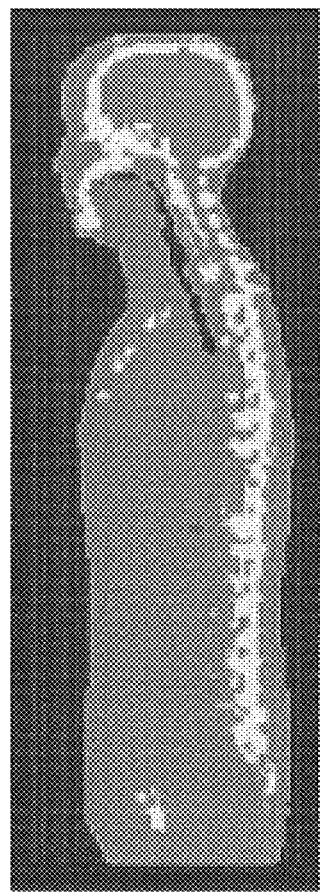
FIG. 3B shows the phantom model of FIG. 3A implemented in Monte Carlo N-particle (MCNP) code.

A demonstration was also made on a Rando® computational model in place of phantom 2. The model was previously developed from a set of CT-scans of the Rando® humanoid phantom. Note that Rando® phantoms are constructed with a natural human skeleton cast inside material that is radiologically equivalent to soft tissue. FIG. 3A shows a 3D reconstruction of the Rando® computational model using a Visualization Tool Kit. The model was implemented in Monte Carlo N-Particle (MCNP) 5 code using lattice and universe options. FIG. 3B shows the model with a voxel size of 0.48×0.48×0.5 cm³.

A source-to-surface distance (SSD) of 88.9 cm was placed on the abdomen area of the Rando® phantom in the place of phantom 2, the area where a prostate is normally located, for example. An exposure was made from the anterior direction. Calculations were similarly performed with the following parameters: 1 cm times the height of the phantom for each beam segment size (total of 9 segments); 1×1×1 cm³ for voxels in the phantom; 1.5×1.5×1.5 cm³ for Responses in EPID 8. Note that the data in parenthesis in FIG. 2 apply to this calculation. The voxel sizes were setup in accordance with the beam divergence and to enhance statistical significance of the calculation. In particular, $\underline{\underline{R}}_P$ was calculated across the entire X-Z plane on a axial slice located at mid-distance from the two ends of Y field size in the Rando® Phantom.

For the calculations, the Monte Carlo N-Particle (MCNP) 5 code was run with F4 mesh tallies for photon. Mesh tallies use superimposed meshes and gives the average flux of a cell in cm² (the same units that F4 tallies use). The calculation time associated with electron tallies is much longer than that with photon tallies. Thus, photon tallies have been used, which is suitable for purposes of demonstration. A variance reduction technique of beam geometry bias was used to reduce the computational time. The mesh card was also modified by using the dose energy (DEn) and dose function (DFn) cards. For photon tallies, the fluence-to-dose-in-water conversion factors were used to transform the output to dose in the unit of MeV per gram. We have used the new mesh tally in MCNP5 instead of the traditional F4 tally due to the ease of input for the user. The mesh tallies allowed us to enter the starting points of the mesh, location of the coarse meshes, and the number of fine meshes within each coarse mesh for the entire simulated geometry instead of having to define such meshes using numerous lattices. The results of the mesh tally were written to a separate output file, and were formatted in a series of 2D matrices (using the OUT keyword) that could be easily analyzed.

Figure 4A:
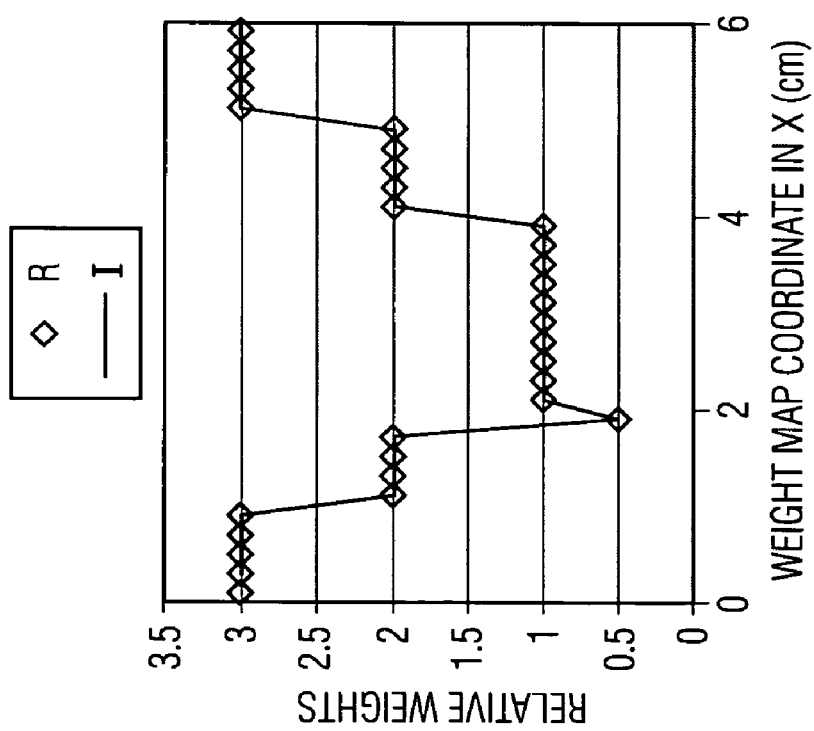
FIG. 4A shows imposed and reconstructed intensity maps designed to create an IMRT inverse pyramid beam.
Figure 4B:
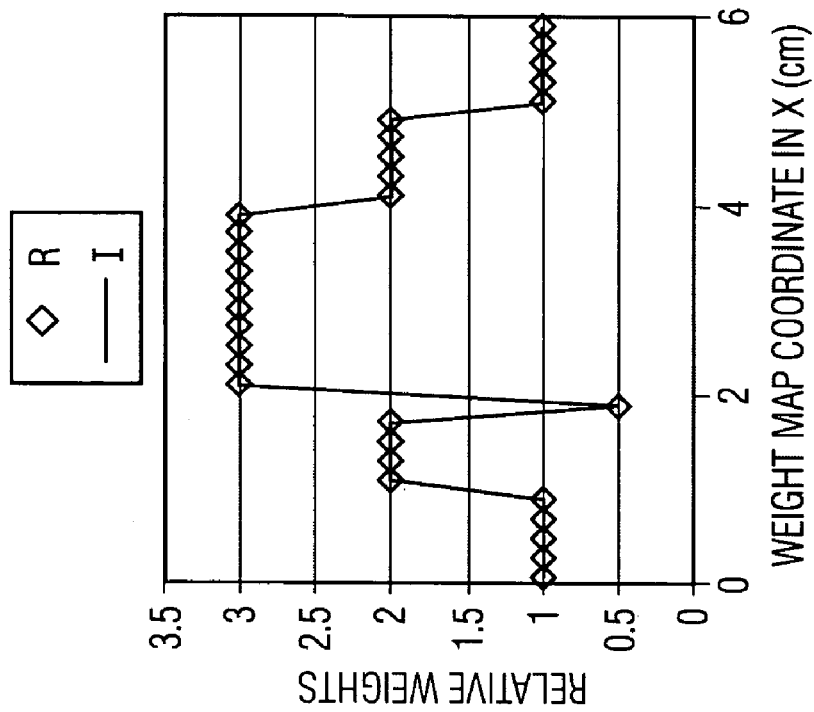
FIG. 4B shows imposed and reconstructed intensity maps designed to create an IMRT pyramid beam.

Using the acquired Responses $\underline{\underline{R}}_E$ and $\underline{\underline{R}}_P$, the dose distributions $\underline{P}$ in the homogeneous phantom 2 and $\underline{E}$ in EPID 8 have been calculated (forward calculation). The beam intensity (Imposed), as shown in FIGS. 4A and 4B, were designed to create two typical IMRT beams for the study with the homogeneous phantom: Pyramid (FIG. 4B) and Inverse Pyramid (FIG. 4A) beams. For these two beams, a delivery error was intentionally created at the position of 1.9 cm or at −1.1 cm distance from the center of the overall field. An intensity reduction of 75% was imposed, in this example. At each voxel in EPID 8, the total dose $\underline{E}$ was calculated by simply weighting $R_E(i,j)$ by the predetermined intensity for each of 30 segments (imposed intensity) and summing them together over the entire segments (see equations (1A-1C) or (2)). This was done without and with the designed error. The intensity $\underline{S}$ without the consideration of the error represents those optimized from treatment planning. The distribution with the error represents treatment delivery which may contain errors, and is to be used for the reconstruction. At each voxel in the phantom 2, $\underline{P}$ was similarly calculated using $R_P(i,j)$ based on equation (5).

On the Rando® phantom, the same procedures were carried out, but with the nine beam segments discussed above. The imposed segmental intensity for the inverse-pyramid beam were three for j=1, 2, 8, and 9; and two for the remaining j's. An additional error scenario was created and imposed by reducing the intensity by 50% from 2 to 1 for j=3. The intensity for the pyramid beam were 1 for j=1, 2, 8, and 9; 2 for the remaining j's. An additional error was similarly designed by changing the intensity by 50% from 2 to 1 for j=3.

Inverse Calculation:

The reconstruction algorithm inherent in equations (3) and (6) was tested. Using the forwardly calculated value of $\underline{E}$ for the case with the error, the beam intensity $\underline{S}$ were reconstructed for the two phantoms and beams. The phantom dose $\underline{P}$ was reconstructed in the midplane of the homogeneous phantom, and $\underline{P}$ was reconstructed in the central axial slice of the Rando® Phantom.

Forward Calculation Results:

For the calculation of $\underline{\underline{R}}_E$ and $\underline{\underline{R}}_P$, MCNP5 simulations were executed using a personal computer equipped with a 2.8-GHz CPU and 1.0-GB RAM under the Linux® operating system. In each of the simulations, 1 million beam particles were used for the homogeneous phantom, requiring 3.4 minutes of computational time. For the Rando® phantom, a total of 30 million beam particles were considered, requiring 90 minutes of computational time. The associated statistical uncertainties for each tally voxel were less than 5-6 and 3% for the homogeneous and Rando® phantoms, respectively. In detail, these values were only for voxels that are in the path of each beam segment, while in all other voxels that received a scattered radiation dose they were greater. Except in the voxels directly neighboring the primary voxels, the doses in the rest of voxels were smaller than that in the primary voxel by two orders of magnitude or greater. Nevertheless, the demonstration intended in this study was not affected by the above statistical accuracy.

Figure 5B:
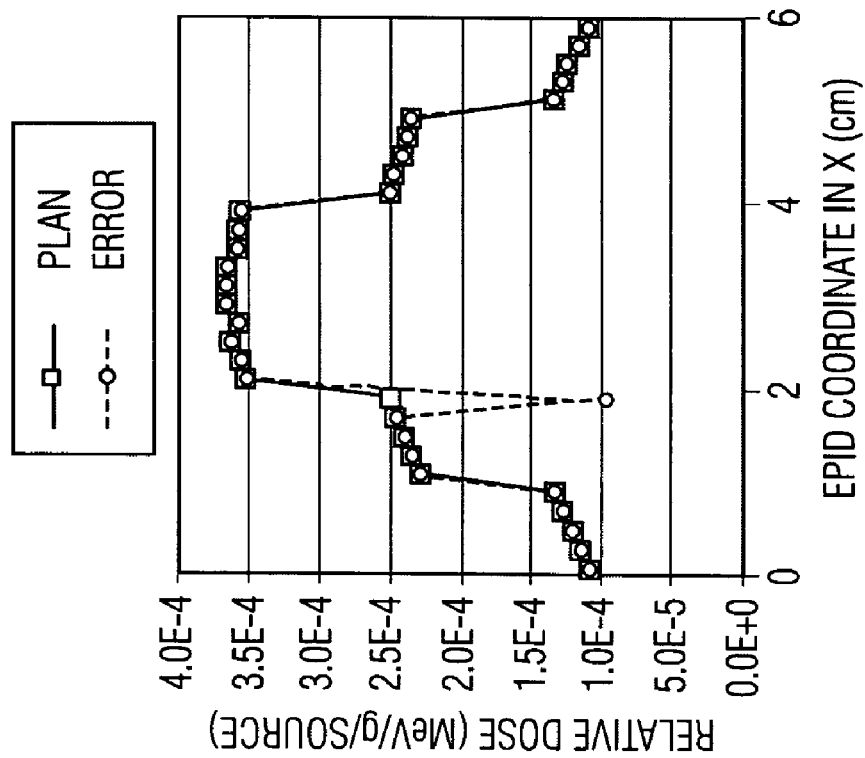
FIG. 5B shows forwardly calculated dose without and reconstructed dose with a designed error in the midplane of a homogeneous phantom from a pyramid beam.
Figure 5A:
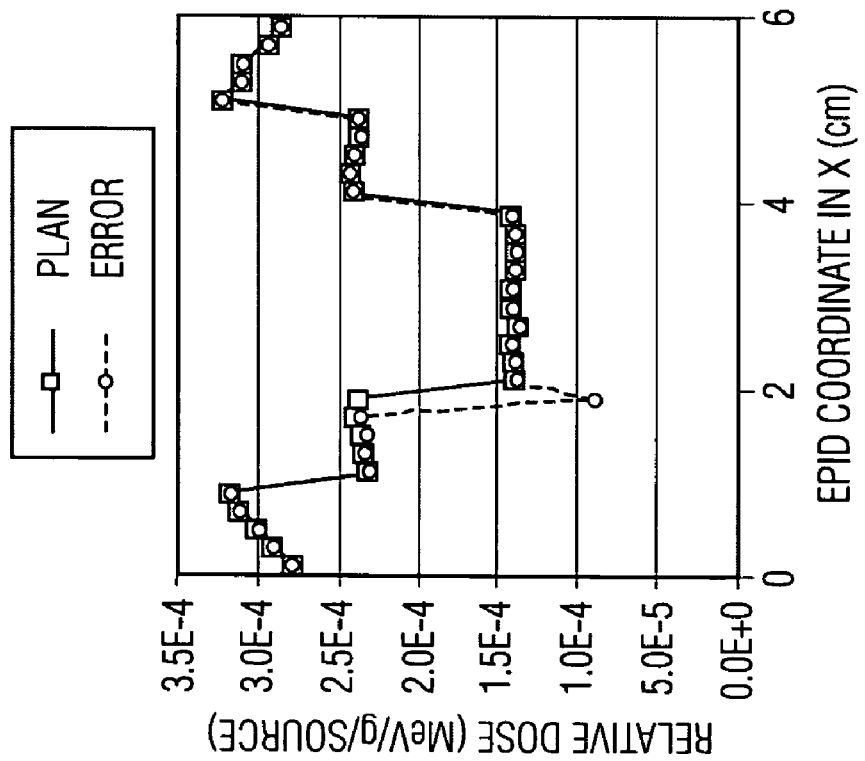
FIG. 5A shows forwardly calculated dose without and reconstructed dose with a designed error in the midplane of a homogeneous phantom from an inverse pyramid beam.

The calculated dose distribution (Plan) in the midplane of the homogeneous phantom 2 is shown in FIG. 5A from an inverse pyramid beam, and in FIG. 5B from a pyramid beam. This figure is explained in more detail in the next section.

FIGS. 6A and 6B (Plan and Error) show the dose deposited in EPID 8 from inverse pyramid and pyramid beams, respectively. Each of these figures show the dose distributions in EPID 8 without and with a designed error in dose delivery. The amount of the dose reduction $\Delta E$ is not as large as that of the intended intensity reduction shown in FIGS. 4A and 4B. This is due to the interference (i.e. in-scattering) from other beam segments irradiated to the locations lateral to the primary.

Inverse Calculation Results:

Inverse reconstruction was carried out as follows. Thirty parallel equations were numerically solved by matrix inversion, as shown by equation (3), using Matlab®. FIGS. 4A and 4B show the reconstructed intensity ($\underline{S}$) compared with the initially imposed intensity for the inverse pyramid and pyramid beams, respectively. Nearly perfect agreement within a few tenths of a percent difference was observed between them. The small error came from the treatment of finite but insufficient effective numbers after decimal points (i.e. rounding off) although in theory an exact solution exists. The difference $\Delta \underline{S}$ is not presented, as it was obvious. The difference can also be directly calculated from $\Delta \underline{E}$ by equation (4). This feature can be useful for delivery evaluation and feedback into the treatment unit for adjustment, particularly when a patient is in the treatment position.

FIGS. 5A and 5B shows the reconstructed dose (Error) in midplane of the homogeneous phantom 2, as previously mentioned. This represents the actual dose delivered to the patient phantom 2 that has received the given treatment, indicated by, and thus reconstructed from the EPID 8 dose. The distribution shows an error at −1.1 cm from the center of the field, which practically can be caused by one or the combination of the several reasons discussed in the beginning. For the same reason discussed above (i.e. interference), the amount of the dose reduction $\Delta \underline{P}$ is not as large as that of the applied intensity reduction.

Figure 7:
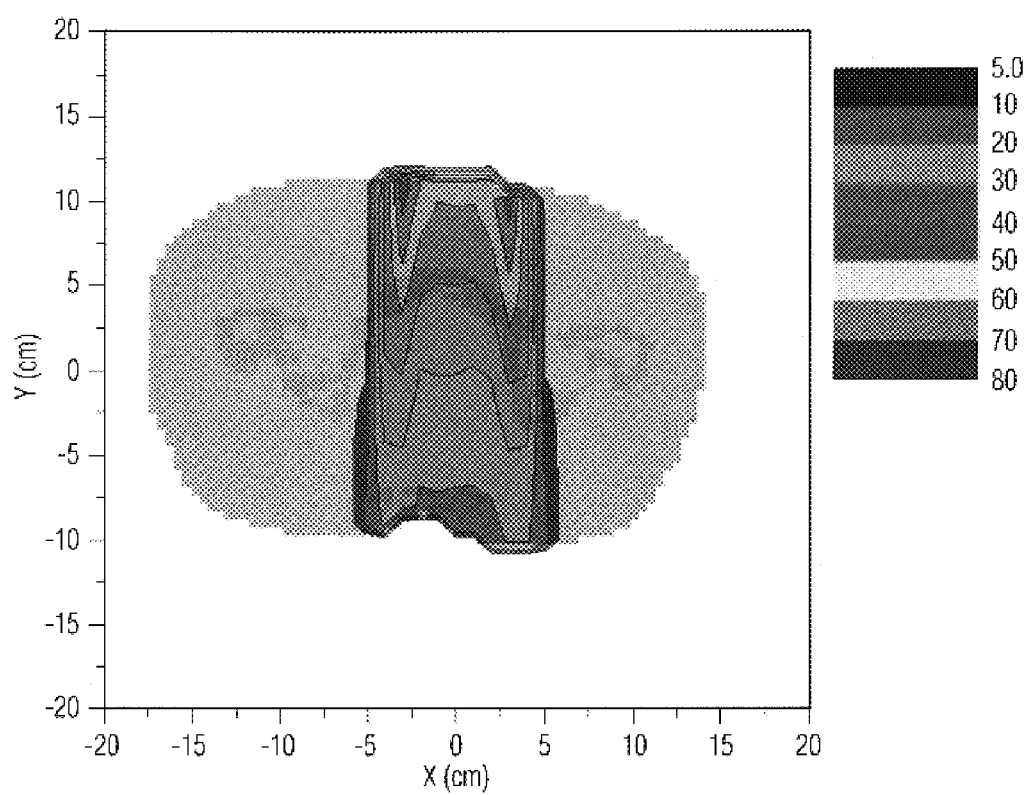
FIG. 7 is the dose distribution in a Rando® Phantom from a inverse pyramid beam without a designed error.
Figure 8:
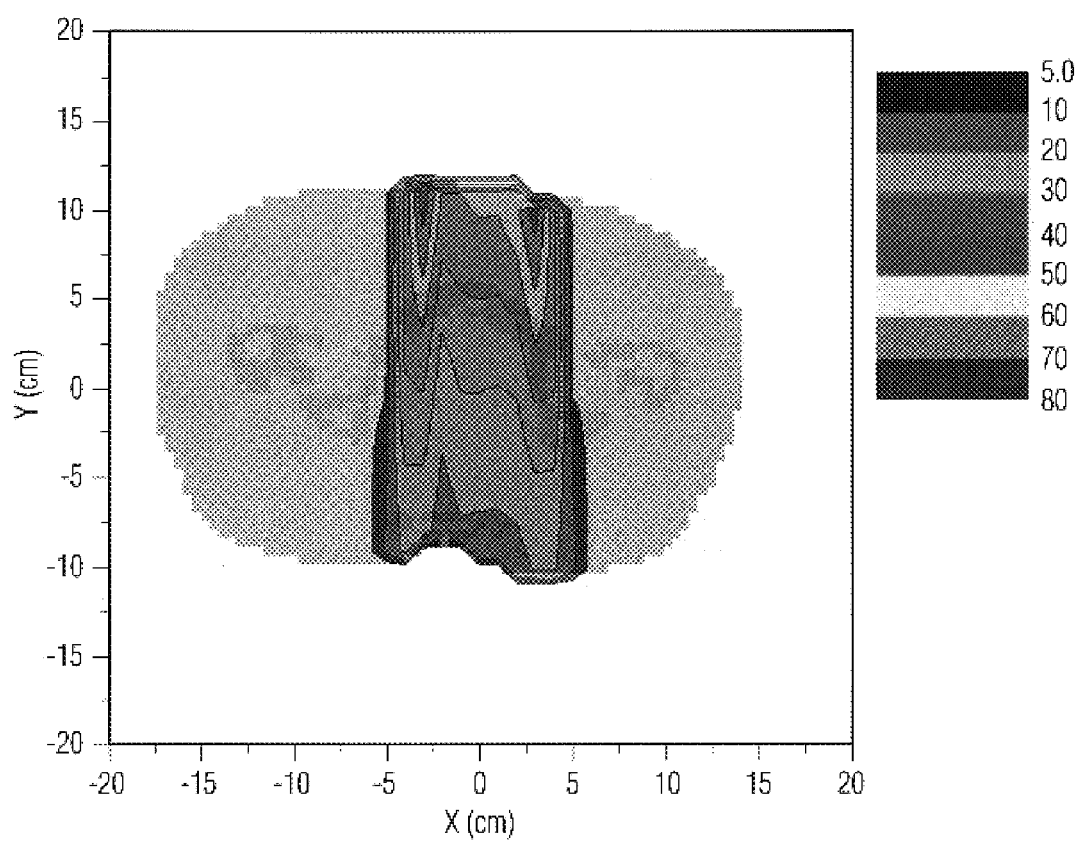
FIG. 8 is the dose distribution in a Rando® phantom from a inverse pyramid beam with a designed error corresponding to an imposed underdose at j=3 or 2.5 centimeters (cm) from the left edge of the field.
Figure 9:
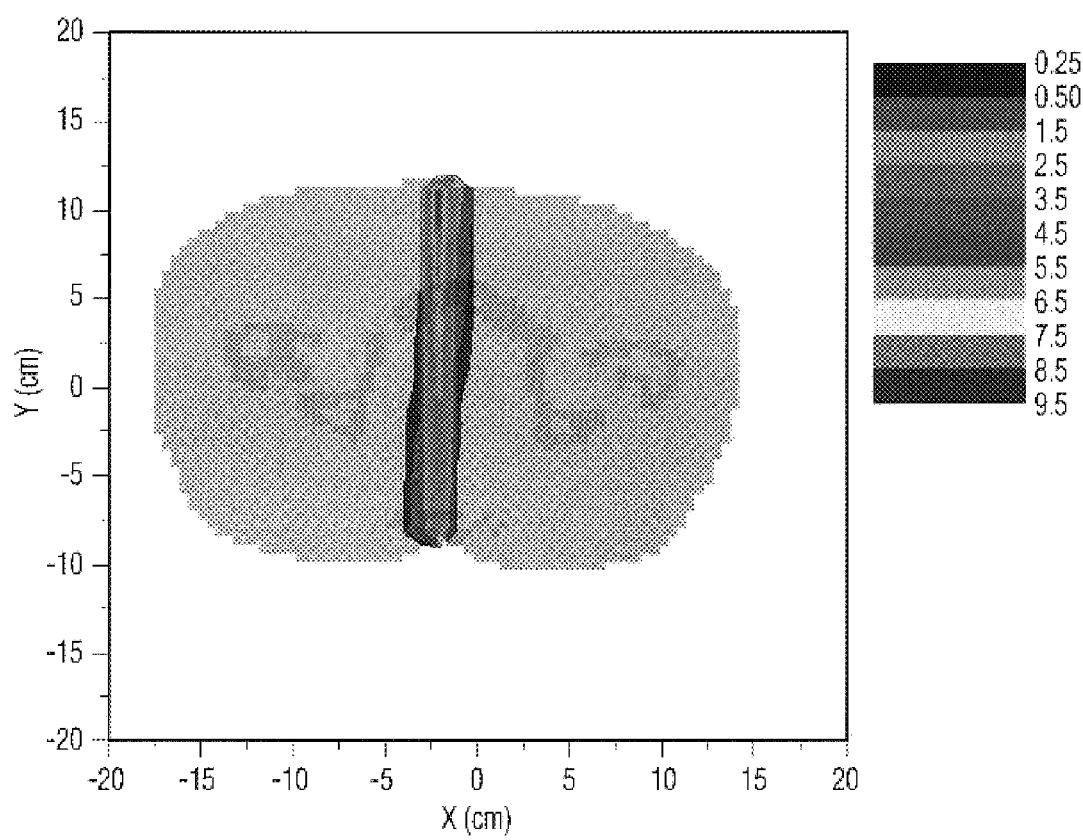
FIG. 9 is the dose difference in a Rando® phantom due to the designed error, the difference being between the dose distributions of FIGS. 7 and 8.

For the case with the Rando® phantom, the beam intensity were successfully reconstructed. The results are not shown herein, as they were very similar to that for the homogeneous phantom in concept. FIG. 7 shows the dose distribution reconstructed for the inverse pyramid beam in the central slice of the Rando® phantom. The legend indicates as follows: 80 equals $80 \times 10^{-6}$ MeV/g/particle and the like. FIG. 8 shows the reconstructed distribution in the same slice where the segmental intensity was reduced at 2.5 cm from the left edge of the field. FIG. 9 shows the difference between the two preceding figures quantifying the dosimetric impact of the designed error. The legend indicates as follows: 9.5 equals $9.5 \times 10^{-6}$ MeV/g/particle, and the like. FIG. 9 does not show the dose corresponding to the designed intensity reduction of 50%. This is due to the in-scattering into the region of interest from the neighboring areas under primary irradiation. The difference $\Delta \underline{P}$ can also be directly calculated from $\Delta \underline{E}$ by use of equation (7). This feature can be useful for delivery evaluation.

Figure 10:
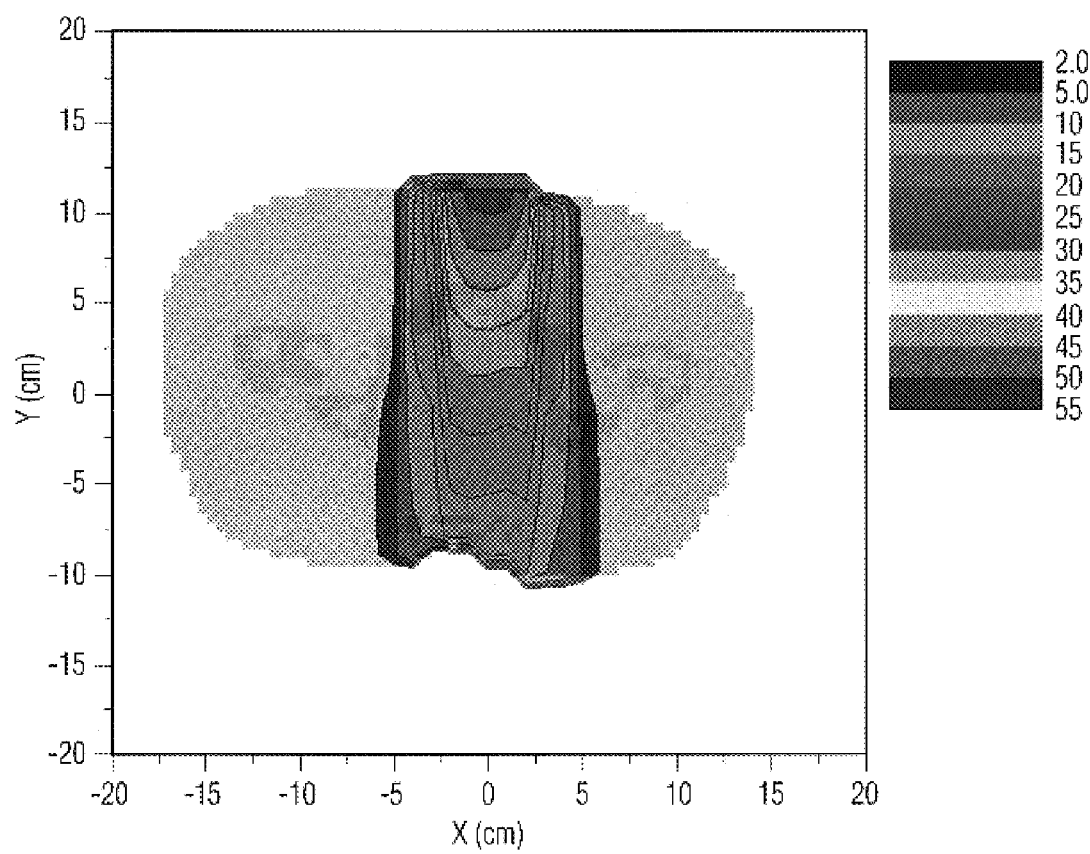
FIG. 10 is the dose distribution in a Rando® phantom from a pyramid beam without a designed error.
Figure 11:
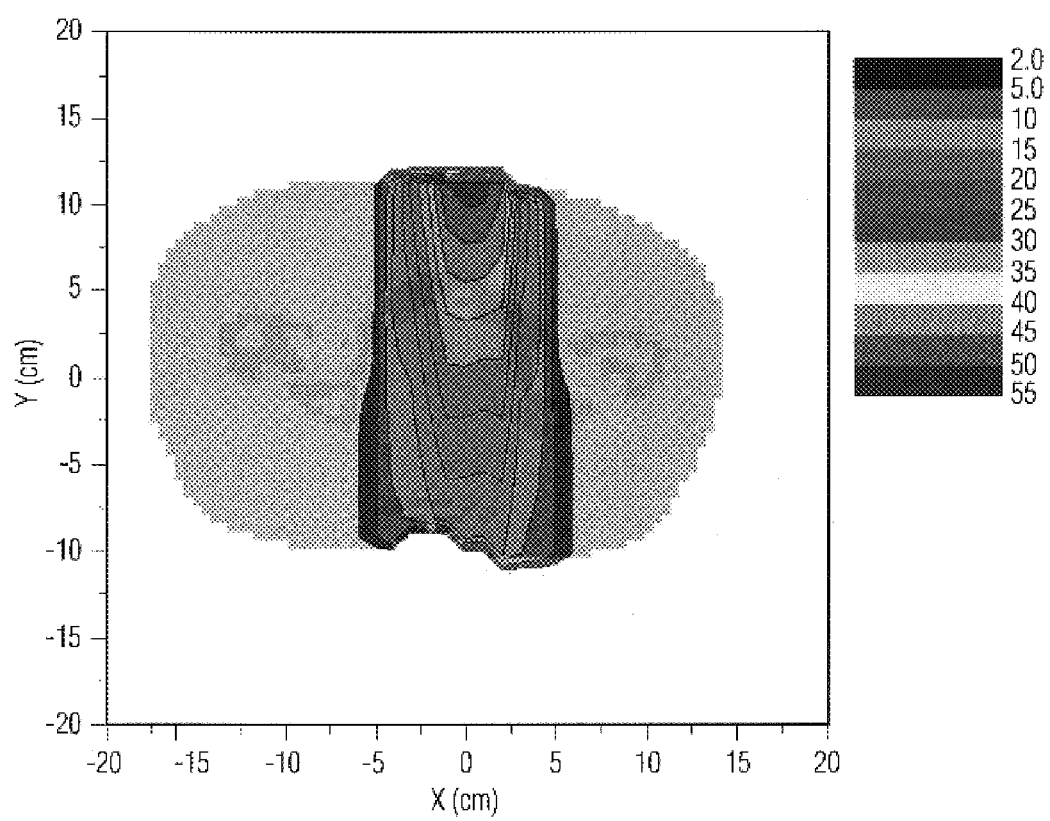
FIG. 11 is the dose distribution in a Rando® Phantom from a pyramid beam with a designed error corresponding to an imposed underdose at j=3 or 2.5 cm from the left edge of the field.
Figure 12:
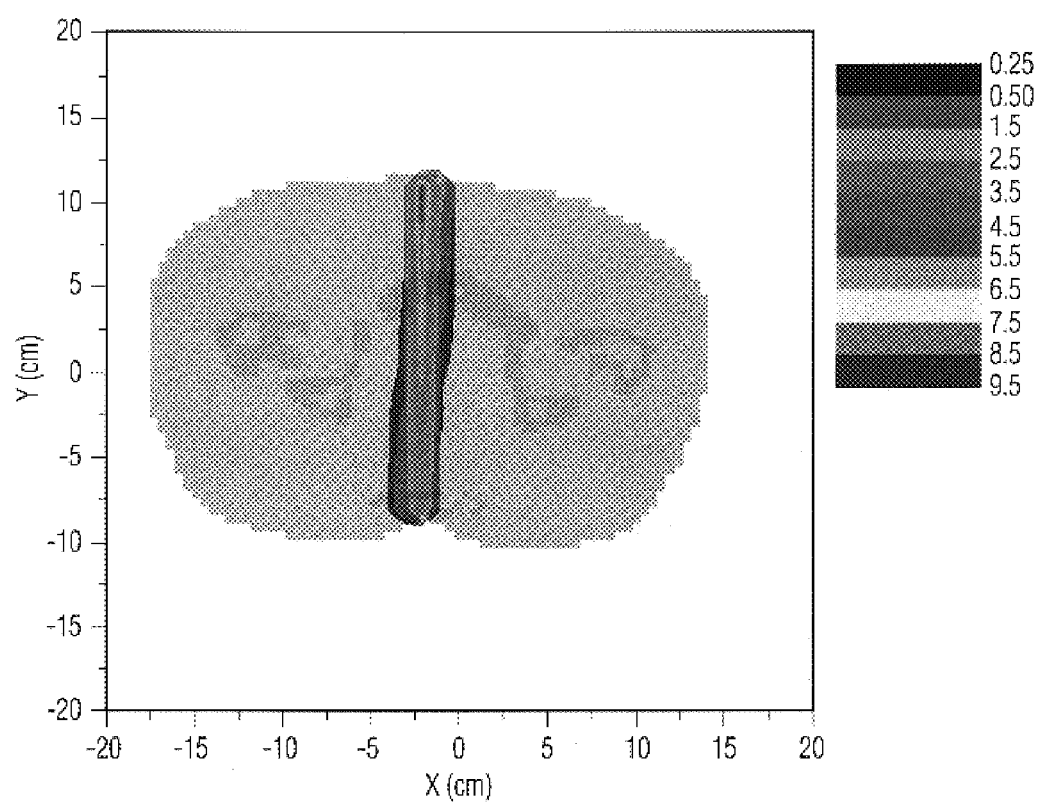
FIG. 12 is the dose difference in a Rando® Phantom due to the designed error, the difference being between the dose distributions of FIGS. 10 and 11.

FIG. 10 shows the distribution reconstructed for the pyramid beam in the central slice of the Rando® phantom. The legend indicates as follows: 55 equals $55 \times 10^{-6}$ MeV/g/particle, and the like. FIG. 11 shows the reconstructed dose distribution on the same slice with imposed underdose at the same position to the above. FIG. 12 shows the difference between FIGS. 10 and 11. The difference on the Rando® phantom due to the planned error corresponded to the imposed underdose at j=3. The legend indicates as follows: 9.5 equals $9.5 \times 10^{-6}$ MeV/g/particle and the like. The imposed intensity reduction of 50% for j=3 did not occur due to interference.

Further Discussions:

The forward MC calculation provides many desirable features to the present method. It potentially enables complete head modeling incorporating non-primary components such as tongue-groove effect, MLC leakage, MLC scatter, and etc. This is particularly important considering the physical situation that the scattered beam components from the beam delivery system hardly reach EPID 8 while they contribute to the patient dose. Accordingly, this signal is not fully contained in the dose image in EPID 8. This problem, therefore, poses a challenge to the idea of using EPID 8 for the dose reconstruction in a patient. It may require secondary treatment of the above components when forward MC calculation is not involved. Furthermore, modeling scatter behind patients as well as calculating portal dose accurately have been an issue for exit dosimetry. This inventive method is free from this issue. Using the forward simulation also eliminates the need of iterative calculation between the planes of EPID 8 and the desired region (phantom 2, and/or a beam plane 40). Finally, MC calculation offers accurate modeling of EPID 8, on which the success of the method derived in this study is based, while convolution/superposition methods suffers from this on a Si-based EPID.

The present method can be implemented in diverse ways in adaptive therapy. One of them is as follows. The calculations were carried out in an axial plane to validate the method. For adaptive verification, however, dose calculations will be performed only in EPID 8, using a real-time image of a patient while he/she is set in treatment position. The dose calculations required include forward calculations of $\underline{E}$ using the beam intensity optimized from treatment planning, $\Delta \underline{E}$ using measurement in EPID, and finally inverse calculations of $\Delta \underline{S}$ using $\Delta \underline{E}$ (equation (4)). Using $\Delta \underline{S}$, an adaptive feedback to the treatment machine will be provided. If desired, this verification can be performed in each fraction of treatment. Three dimensional dose reconstruction requiring longer calculation time can then be finished after each treatment.

Although a completely different area of study, to adequately account for clinical situation, modeling of the internal uncertainties due to inter- and intra-fraction organ motion and deformation has to be considered. Anatomical information from on-line imaging will be of a great assist. After the reconstruction is performed, the discrepancy between the distributions from the planning (on the image previously acquired) and the treatment delivery (on the image acquired in treatment condition) can be quantified. Matching the anatomical information of a patient between the two stages is of assistance. This discrepancy can be accounted for in the treatment planning for later fractions. This is to achieve the clinical goal of dose uniformity in the target and saving of critical organs that may have been and can be underachieved due to the various uncertainties discussed in the introduction.

While the MC calculation has the above merits, it suffers from relatively long calculation time. The calculation speed is essential for the real-time clinical implementation of this method. To speed up the calculations, the use of computers with multiple-cluster CPUs will facilitate simultaneous multiple processing for all beam segments typical of IMRT. This strategy is ideal for IMRT. In addition, the appearance of faster MC algorithms will speed up the computation dramatically. In our separate calculations using one of the faster algorithms, the calculations in a voxel with the size of $0.2 \times 0.2 \times 0.5$ cm$^3$ at the depth of 10 cm in a flat phantom and a voxel with the same size in EPID phantom consumed less than a minute. Therefore, the present method of this study promises to be a potentially useful tool for IMRT verification.

Two-Dimensional Validation:

The above one-dimensional demonstration validated the method of the present invention. In the following, the present method is demonstrated in a realistic situation where IMRT beams are modulated two dimensionally. This two-dimensional validation is important to test computational feasibility of the inventive method.

Figure 13:
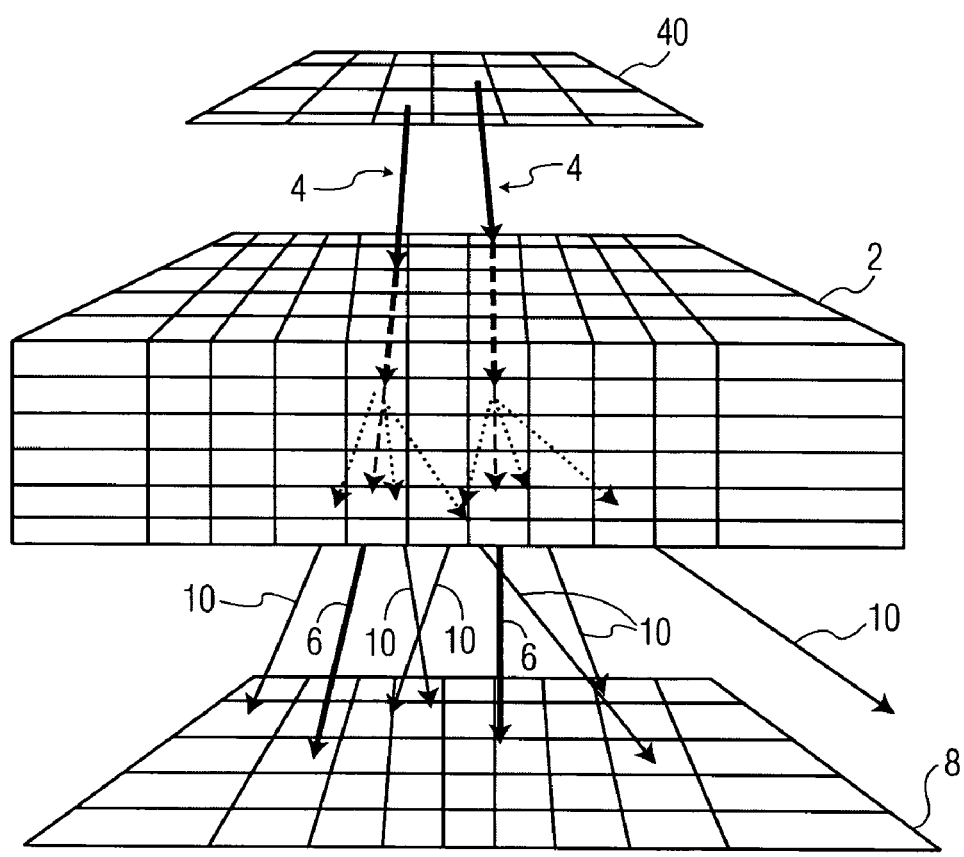
FIG. 13 is a block diagram showing a two-dimensional computational model of a treatment system and radiation transport process for an embodiment of the invention.

FIG. 13 shows a two-dimensional representation of radiation transport involved in the inventive method. The segmented beam 4 is emitted from the intensity plane 40 unto a homogeneous patient phantom 2 and energy is deposited. The attenuated primary beam 6 and scattered radiation 10 leave the patient phantom 2 and enter into EPID 8.

Figure 14A:
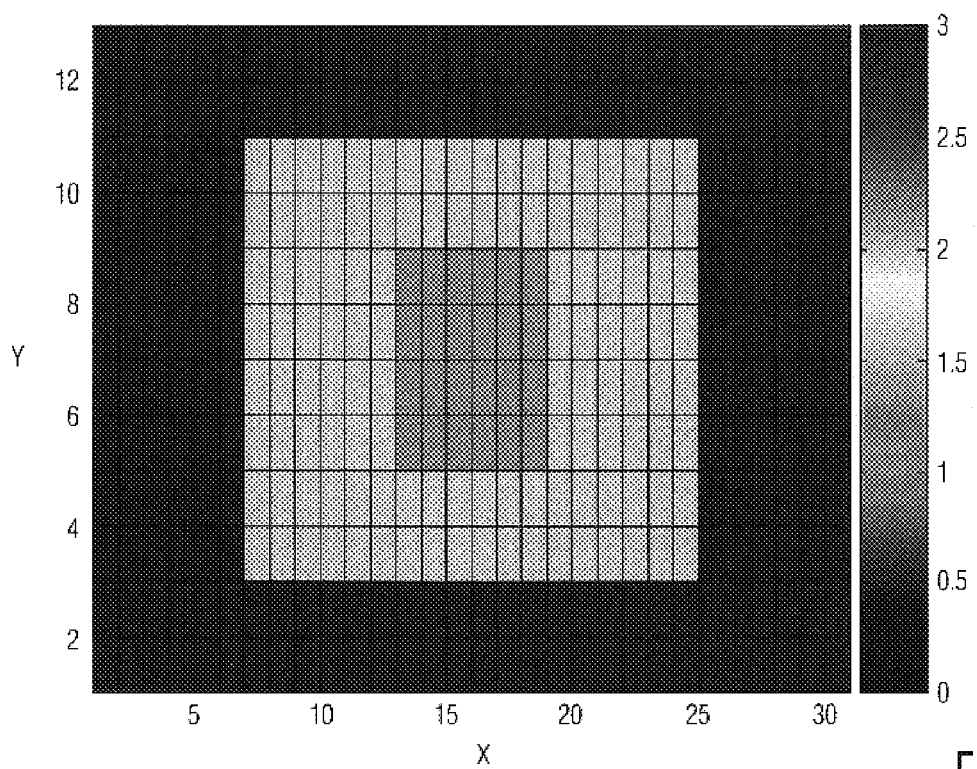
FIG. 14A is the imposed beam intensity map for an inverse pyramid beam without any error designed.
Figure 14B:
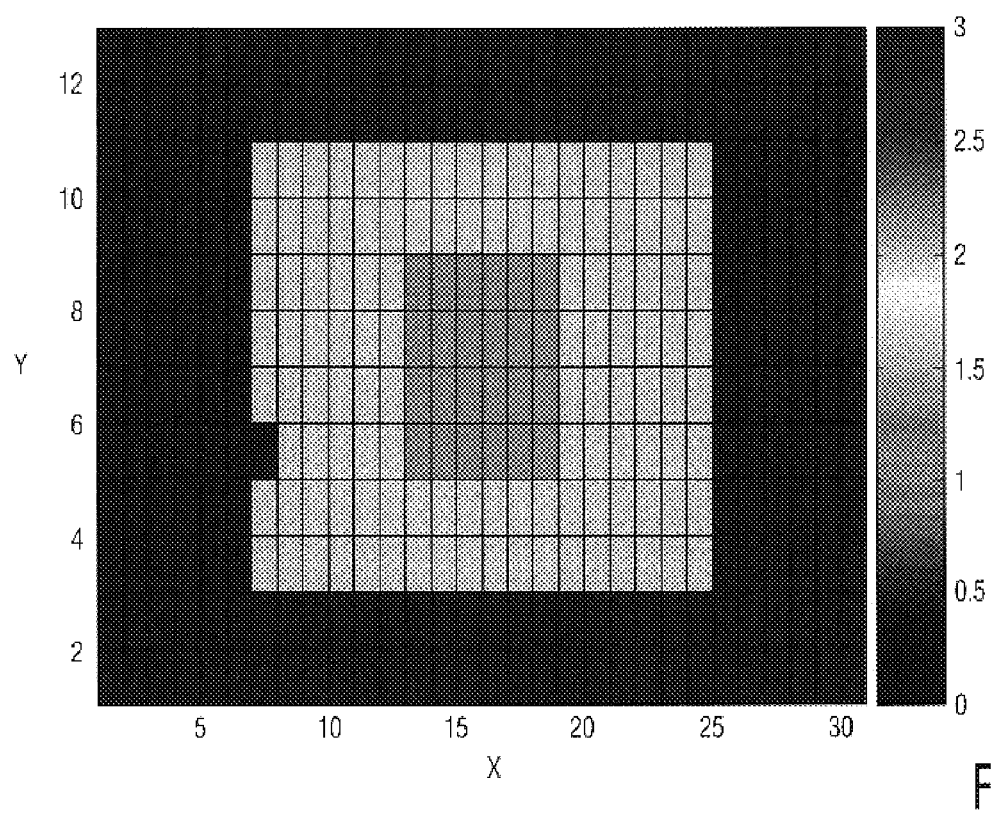
FIG. 14B is the imposed beam intensity for an inverse pyramid beam with a designed error.
Figure 15:
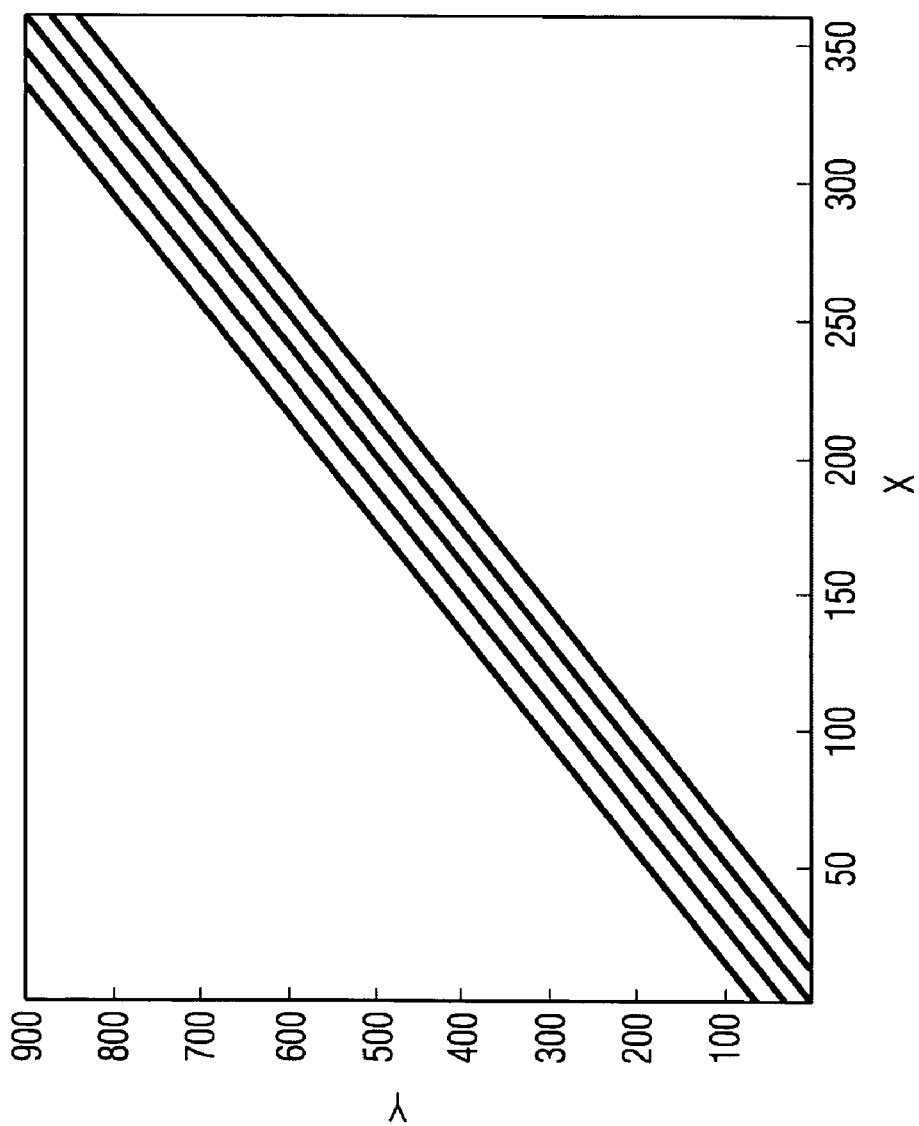
FIG. 15 is a graphical representation of the matrix of $\underline{\underline{R}}_P$.

The test case taken in this study includes 30×12 (6×6 cm$^2$) beam segment matrix, shown in FIGS. 14A and 14B, which involve a 360×1296 matrix for $\underline{\underline{R}}_E$ and 360×900 matrix for $\underline{\underline{R}}_P$. The selection of 30×12 mesh corresponds to the tolerance of collimator positional error (2 mm) based on the AAPM TG 40 report and the width of a Varian Millennium MLC (5 mm), respectively. Therefore, the unit beam segment mesh size was 0.2×0.5 mm$^2$. The unit scoring voxel size was 0.2×0.2×0.5 mm$^3$ within the phantom and EPID and it extends the horizontal area of 20×20 cm$^2$. The responses were calculated in the midplane of 20 cm thick phantom placed at 100 cm SAD and that of 2 cm EPID phantom at 120 cm. FIG. 15 shows the matrix diagram of $\underline{\underline{R}}_P$ where the value is largest along the diagonal axis due to primary dose deposition and it diminishes due to scatter dose deposition as coordinates move away from the diagonal axis.

Pyramid and inverse pyramid dose distributions were constructed by convolving a combination of three source weights of 1, 2, and 3, distributed across the intensity map shown in FIG. 14A with the determined Responses. An accident involving the change in intensity by 1 was designed at (7.5) point in the source map (see FIG. 14B).

Figure 16:
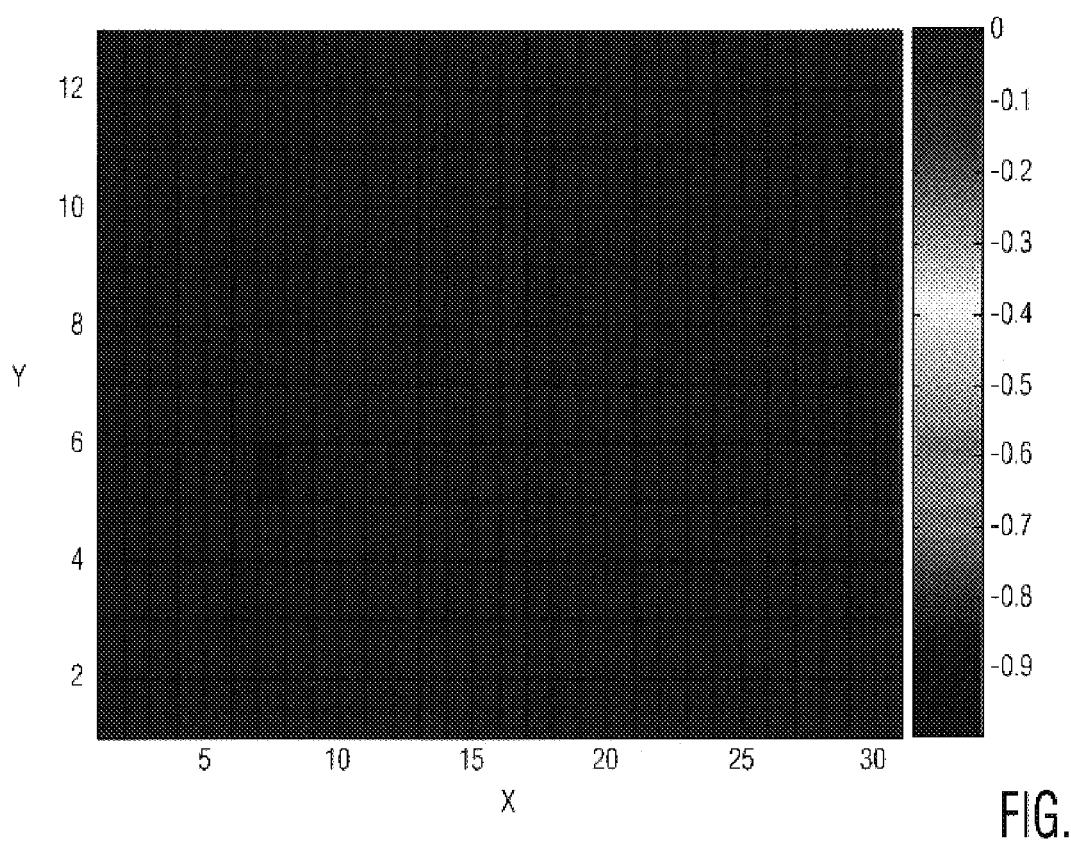
FIG. 16 is the reconstructed beam intensity difference for an inverse pyramid beam.
Figure 17:
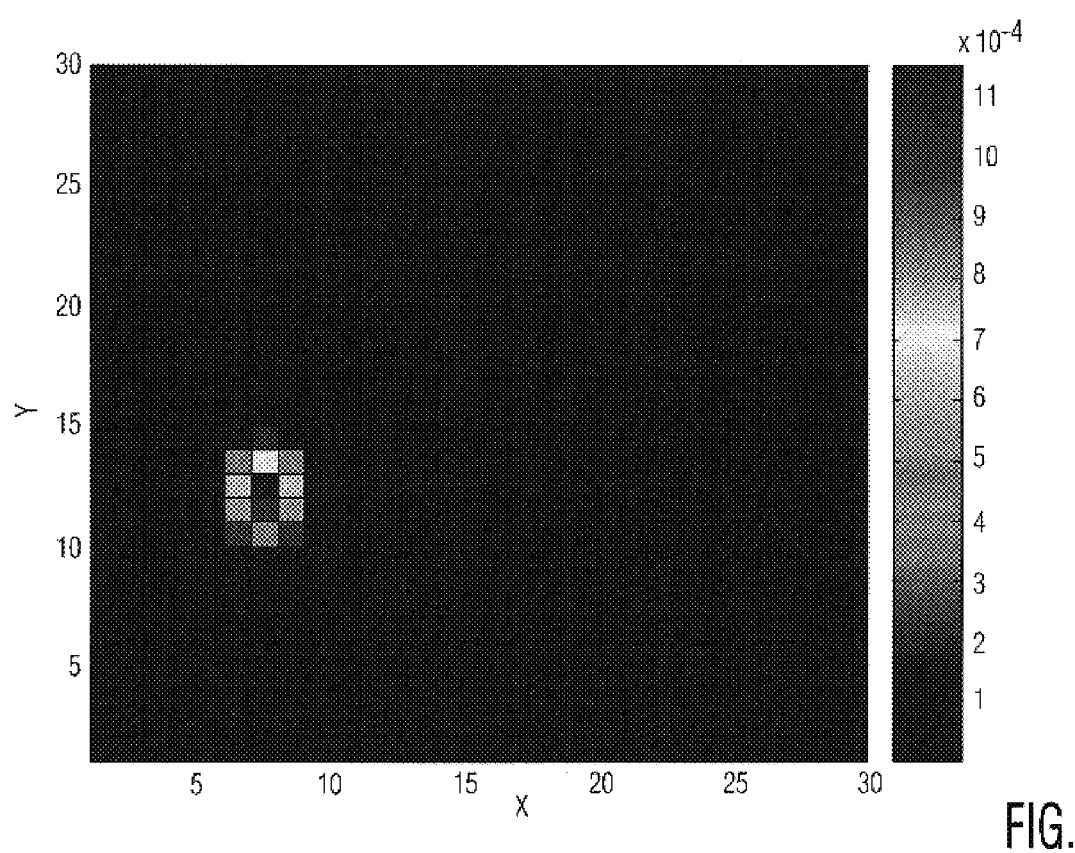
FIG. 17 is the reconstructed dose difference on the central plane of a 20 cm thick phantom due to the designed error for an inverse pyramid beam.
Figure 18:
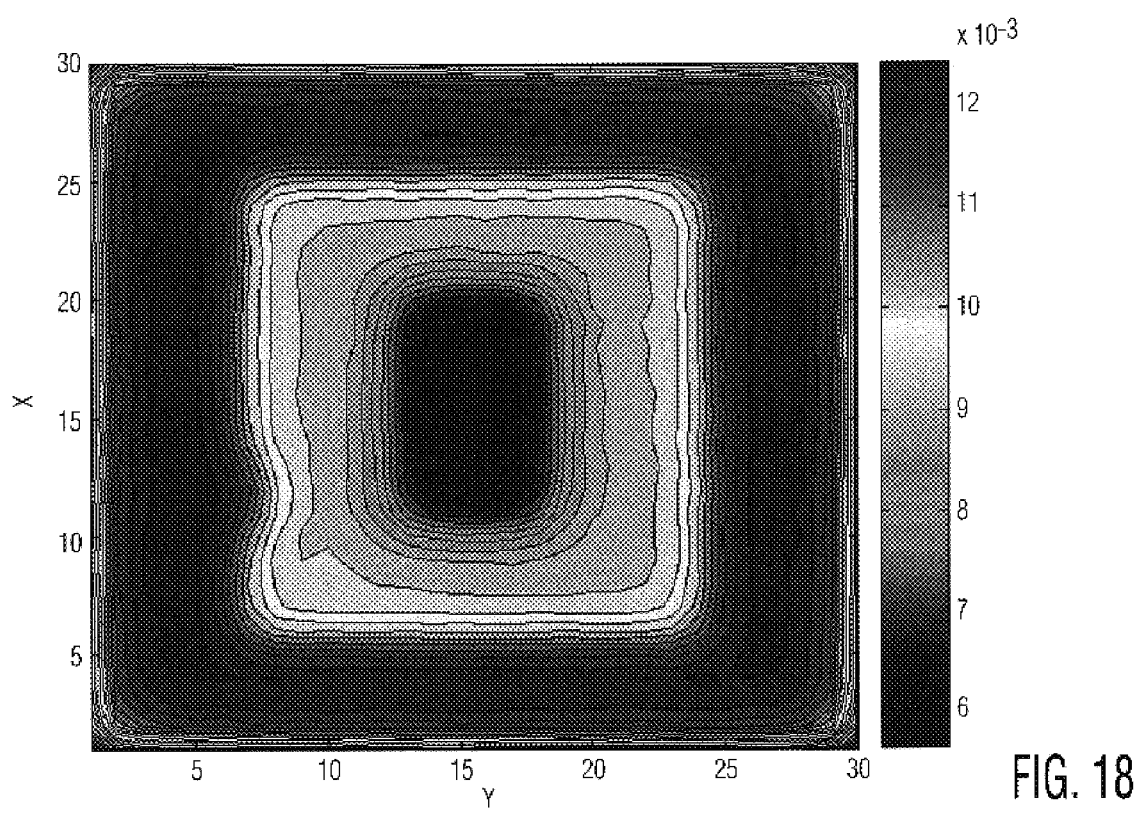
FIG. 18 is the reconstructed dose distribution delivered on the central plane of a 20 cm thick phantom.
Figure 19:
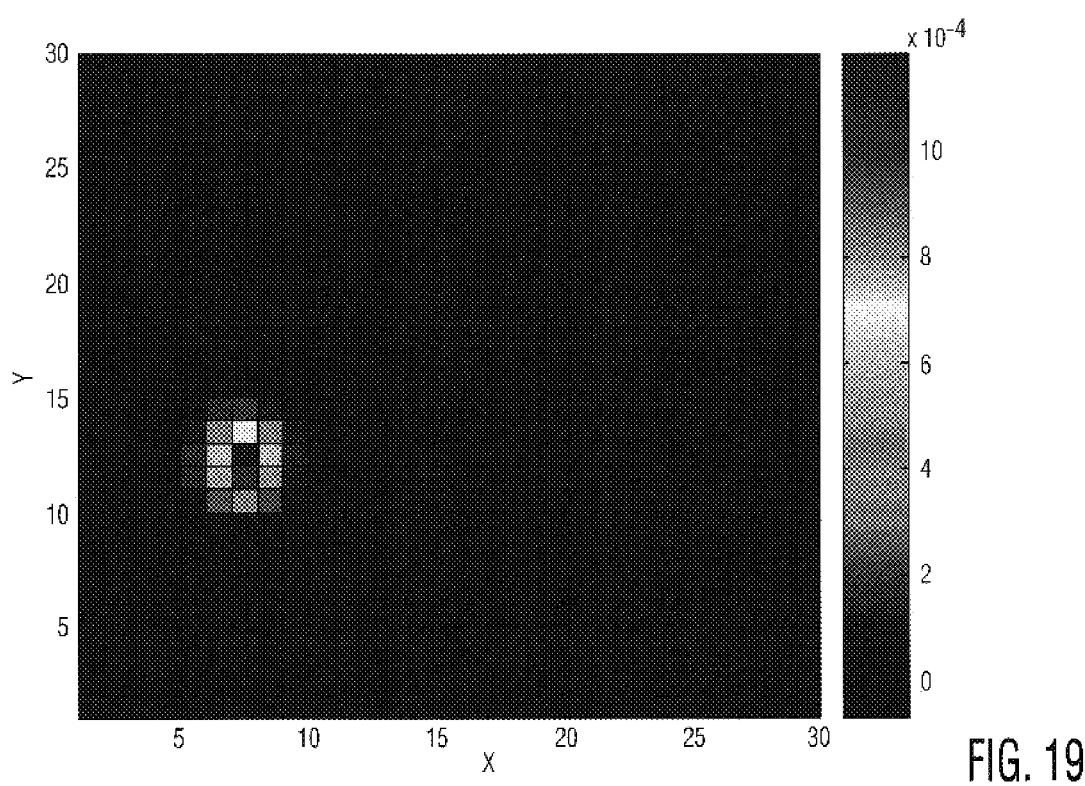
FIG. 19 is the reconstructed beam intensity difference for an inverse pyramid beam when an alternating noise of +/−1% among the dose images in neighboring voxels in the EPID was assumed.

Forward calculation of $\Delta\underline{E}$ due to the accident was done using eq. (1), simulating forward clinical process. Using eq. (4), $\Delta\underline{S}$ was calculated to be −1 at the designated location for the inverse pyramid beam from $\Delta\underline{E}$ (FIG. 16). Negligible error was obtained only due to data rounding off. Similarly, using eq. (7) $\Delta\underline{P}$ was calculated for the inverse pyramid beam (FIG. 17). The MC run for each beamlet took 1 minute using XVMC code. The data for the pyramid beam was omitted. For all of these matrix calculations, using a Pentium 4 personal computer with 2.8 GHz CPU less than 10 seconds of calculation time and 10 MB of memory were used. The data in FIG. 17 can be fed back into a treatment planning system for the adaptive planning of the later treatments. FIG. 18 shows the dose distribution on the central plane of the phantom showing misdelivery due to the designed error. FIG. 19 shows the dose difference distribution when the dose image in EPID E contains electric noise as much as +/−1%. FIGS. 17, 18, and 19 are provided in the unit of Gray normalized to a unit beam particle per beamlet. FIG. 19 shows that the method works well with real situations involving measurement and thus noise. Therefore, the inventive method was validated for clinically-relevant two-dimensional implementation.

Conclusion:

The illustrated dose reconstruction algorithm has been validated. For this validation, it was necessary to generate a dose distribution in EPID 8 using a forward MC calculation, which incorporated an error designed therein. From this distribution, it has been demonstrated that IMRT can be inversely verified and the dose distribution in a patient can be reconstructed. Therefore, the inventive method is useful for verifying IMRT delivery that can be affected by uncertainties associated with MLC positional reproducibility and beam output stability.

It has been shown that the present method does not use any iteration between the planes of EPID 8 and beam or patient 22, as in theory it warrants a unique solution. Among many desirable features associated with this method, one promising feature is that this method can fully utilize the beam modeling as accurately as it actually is.

Figure 20:
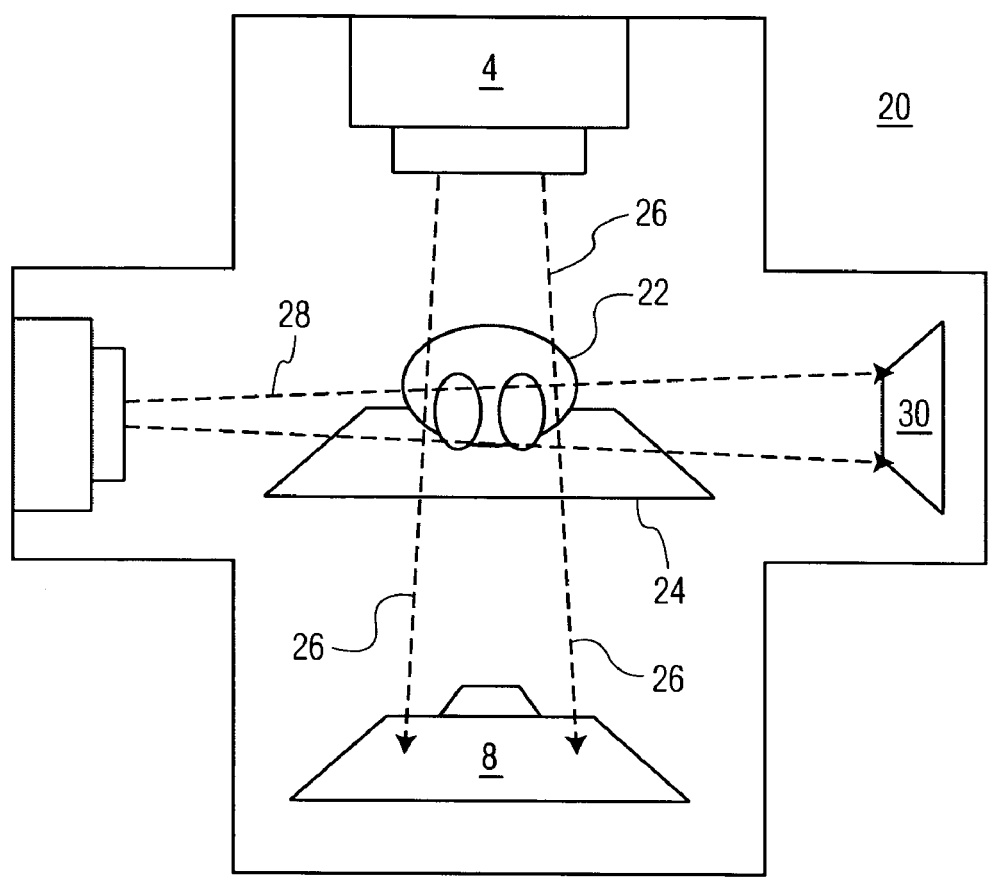
FIG. 20 is a block schematic diagram showing a linear accelerator with therapeutic x-ray delivery and imagining systems in use with a patient for an embodiment of the invention.

Using the Invention:

Actual use of the present invention will now be described with reference to the above-described various embodiments and proof of operation of the invention. In FIG. 20, a simplistic block schematic diagram is shown of a typical linear accelerator with therapeutic x-ray delivery and imaging system 20. The system 20 includes a megavoltage (MV) x-ray beam 26, and an electronic portal imaging device (EPID) 8, the latter being positioned beneath a patient 22 positioned on a treatment couch 24, for receiving an x-ray radiation dose. Typically, an x-ray dose is emitted from the x-ray beam 26, in a manner focusing the x-ray beam to impinge upon and kill cancerous tissue within the patient 22. The EPID 8 is positioned to detect the transmitted radiation dose image after passage through the cancerous tissue and patient 22 during treatment. The emitted x-ray beams 26 also pass through the treatment couch 24 without affect. Also included in the x-ray delivery system 20 is an imaging provided by a kilovoltage (kV) x-ray beam 28 for emitting low-level x-rays to a patient 22, which after passing through the patient 22 are detected by a kV x-ray detector 30, in order to provide an anatomical image of the patient 22 during treatment. The latter is known in the art as treatment imaging, and is functionally equivalent to images provided by a computer tomography (CT) system. As shown, the MV x-ray beam 26 is mounted orthogonally to the kV x-ray beam 28 and kV detector 30, the latter two being in horizontal alignment with one another. The system 20 in a preferred embodiment of the invention is suitable to provide precision therapy such as an intensity modulated radiation therapy (IMRT). However, as previously mentioned, the method of the present invention can be employed with other than a treatment modality of IMRT.

Figure 21:
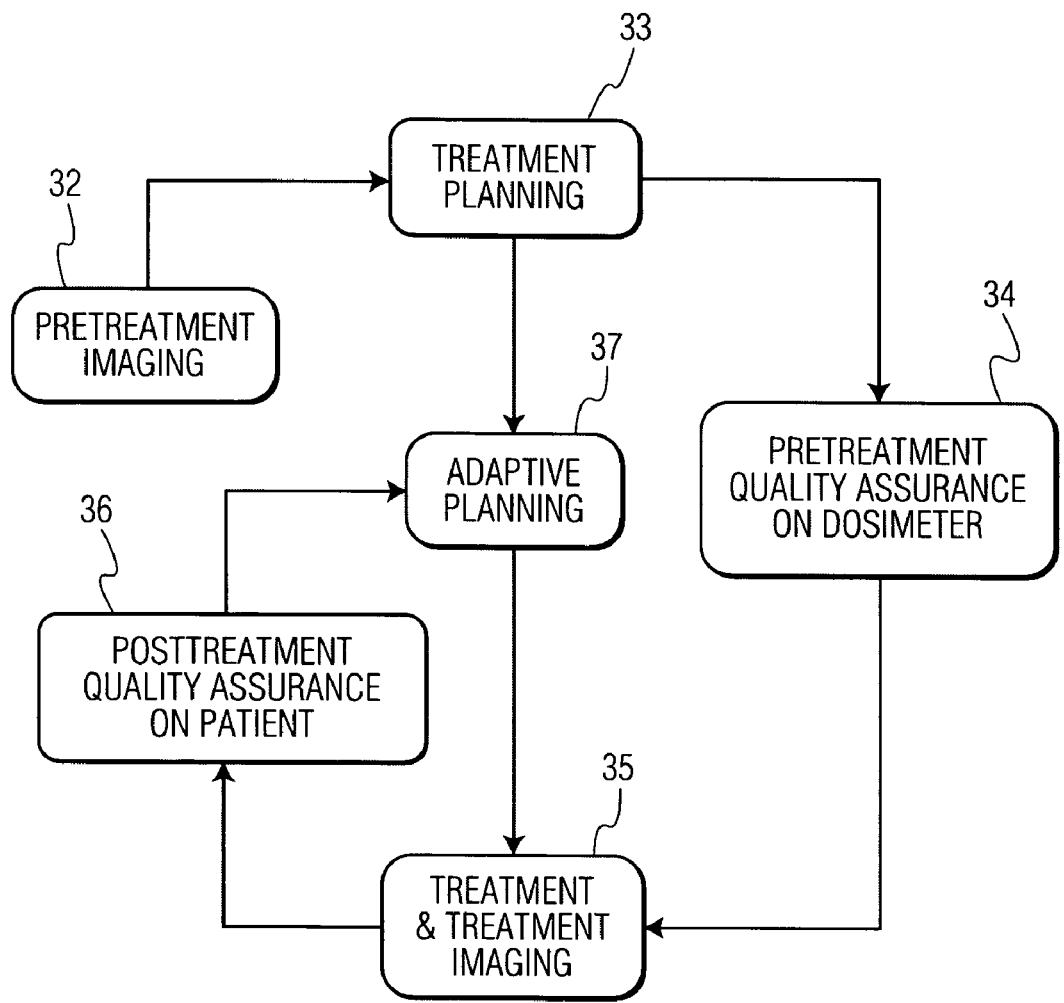
FIG. 21 is a flowchart or flow diagram illustrating the steps involved for a radiation therapy procedure for a preferred embodiment of the invention.

In FIG. 21, a flowchart is shown for detailing the various steps involved in the method of the present invention. More specifically, as shown, the present method begins with the pretreatment imaging step 32 for imaging a patient. In a preferred embodiment, the imagining is carried out through use of computer tomography (CT), for example. Step 33 for treatment planning involves utilizing the pretreatment image from step 32 and the computerized planning megavoltage radiation delivery via system 20, for example. The computerized planning involves finding a target within the patient image and more importantly optimizing the radiation delivery to the determined target. In doing so, the treatment planning step 33 determines incident angles and intensity of radiation beams for application to the patient image including the target. As is known in the art, IMRT systems typically include a multi-leaf collimator (MLC) for configuring the beam collimation, whereby the treatment planning step 33 determines MLC motion, dwell position, and dose rate in instances where IMRT is delivered. Typically, IMRT treatment requires the verification of the radiation dose delivered, whereby the verification is typically made by measurement on a phantom before actual x-ray treatment of a patient, and the actual x-ray transmission or delivery may not be directly representative of planning made in step 33. Such verification of radiation before treatment, commonly known as pretreatment quality assurance as shown by step 34 must be utilized in order to safeguard a patient from inaccurate dose delivery different from the planning. The inaccuracy originates from inaccurate dose calculation in planning, limitations in dose delivery such as MLC positional error and/or reproducibility, output x-ray beam magnitude fluctuation, and so forth. In fact such verification is required by health insurance companies in the U.S. as a pretreatment requirement for billing purposes. The verification procedure typically includes calculation of the radiation dose from a predetermined x-ray beam transmitted through a flat phantom in accordance with the prior treatment planning for a particular patient. Allaying such calculation or simulation, an identical flat phantom which contains a dosimeter is positioned in place of a patient 22 in the x-ray delivery system 20, and the planned x-ray beam is transmitted through the flat phantom to permit measurement of the radiation dose in the flat phantom against the planned radiation dose. If the measured dose is substantially the same as the planned radiation dose, then verification is considered successful, and actual treatment of the patient is initiated, in this example by positioning the patient 22 on the treatment couch 24, as shown in FIG. 20. As previously indicated, as part of the treatment of the patient 22, the on-board imaging system of the therapeutic x-ray delivery system 20 is used to obtain an image of the patient under treatment, for providing anatomical information relative to the patient 22 via the treatment imaging step 35. This involves operation of the kilovolt x-ray beam 28 for passing low-level x-rays through the patient 22 to a kilovoltage x-ray detector 30, for obtaining the images. The image obtained in the treatment imaging step 35 may turn out to be different from the pretreatment image acquired in pretreatment imaging step 32. So, the requirement of the pretreatment verification is not sufficient enough to ensure accurate radiation delivery to a patient. This is where the inventive method contributes. In the natural treatment of the patient during step 35, the EPID 8 positioned under the patient 22 provides measured radiation dose images from the radiation that has passed through the patient 22 as previously described. Inverse verification of the actual radiation dose delivered to a target within the patient 22 is then calculated through use of equation (6) by using the dose images from EPID 8 and the patient image obtained during treatment. As previously described above, the method of the present invention provides non-iterative, direct dose reconstruction. By comparing the dose distributions developed during the treatment planning step 33 with the inversely calculated dose reconstruction carried out in the post treatment quality assurance step 36, one can determine whether the patient 22 received a planned radiation dose, or an overdose, or an underdose throughout the target and the rest of patient image obtained in step 35. It should be noted that the differences in the pretreatment CT step 32 and treatment images of the patient obtained in step 35 must be accounted for through deformable organ image registration. The quantified amount of overdose and underdose is necessarily provided as an input for new treatment planning of further radiation dose treatments for the patient 22. In this manner, the treatments that must be carried out over a plurality of time spaced apart radiation dose treatments for a total cumulative dose distribution as planned can be substantially obtained. In this manner, individual treatment radiation dose delivery errors can be negated. The procedure is typically repeated until the total planned radiation dose has been delivered to the patient 22. Note that after verification of the radiation delivered to a patient in step 36, an adaptive planning step 37 is entered. Particularly, where IMRT is utilized, adaptive planning step 37 is utilized for determining whether the next planned radiation for the patient 22 must be increased or decreased in accordance with any detected under dosing or over dosing, respectively from step 36. When an IMRT treatment is utilized, it is preferred that from the adaptive planning step 37 the pretreatment quality assurance step 34 is entered into, followed by steps 35, 36, and 37. Depending on how accurate IMRT delivery and/or adaptive planning is, step 35 can immediately follow step 37. As indicated, over the course of time required for providing successive radiation doses over spaced apart treatment for a patient 22, steps 34 through 37 are typically repeated as a circular procedure of adaptive therapy until a total planned cumulative radiation dose has been delivered to the patient 22.

Although various embodiments of the invention have been shown and described, they are not meant to be limiting. Those of skill in the art recognize certain modifications to the various embodiments of the invention, which modifications are meant to be covered by the spirit and scope of the appended claims.

What is claimed is:

1. A method for verifying radiation therapy in a therapeutic x-ray delivery system for transmitting radiation doses in the form of an x-ray beam or beam segments, said method comprising the steps of:

inversely calculating the radiation dose received by a phantom or patient comprising the step of solving the following equation:

$$\underline{P} = \underline{\underline{R}}_P \underline{\underline{R}}_E^{-1} \underline{E}$$

where $\underline{P}$ is the vector of P, P is the dose in a phantom, $\underline{\underline{R}}_P$ is the matrix of $R_P$ (beam-to-phantom Response), $\underline{\underline{R}}_E^{-1}$ is the inverse matrix of $R_E$ (beam-to-EPID Response), and $\underline{E}$ is the vector of E, and E is the measured dose in EPID.

2. The method of claim 1, wherein said calculating step further includes the step of solving the following equation:

$$\Delta \underline{P} = \underline{\underline{R}}_P \underline{\underline{R}}_E^{-1} \Delta \underline{E}$$

where $\Delta \underline{P}$ is the vector for the difference between planned (forwardly calculated using planned S) and reconstructed doses in a phantom or patient, $\underline{\underline{R}}_P$ is the matrix of $R_P$ (beam-to-phantom Response), $\underline{\underline{R}}_E^{-1}$ is the inverse matrix of $R_E$ (beam-to-EPID Response), and $\Delta \underline{E} = (\underline{E}^{predicted} - \underline{E}^{measured})$, where $\underline{E}^{predicted}$ is the vector for forwardly calculated dose in EPID and $\underline{E}^{measured}$ is the vector for measured dose in EPID.

3. The method of claim 1, wherein said calculating step further includes the step of solving the following equation:

$$\underline{S} = \underline{\underline{R}}_E^{-1} \underline{E}$$

where $\underline{S}$ is the vector of S, a beam intensity map, $\underline{\underline{R}}_E^{-1}$ is the inverse matrix of $R_E$ (beam-to-EPID Response), $\underline{E}$ is the vector of E, and E is the measured dose in EPID.

4. The method of claim 1, wherein said calculating step further includes the step of solving the following equation:

$$\Delta \underline{S} = \underline{\underline{R}}_E^{-1} \Delta \underline{E},$$

where $\Delta \underline{S}$ is the difference between the imposed and reconstructed intensity, $\underline{\underline{R}}_E^{-1}$ is the inverse matrix of $R_E$ (beam-to-EPID Response), and $\Delta \underline{E} = (\underline{E}^{predicted} - \underline{E}^{measured})$, where $\underline{E}^{predicted}$ is the vector for forwardly calculated dose in EPID and $\underline{E}^{measured}$ is the vector for measured dose in EPID.

5. The method of claim 1, wherein said calculating step further includes the step of acquiring $\underline{\underline{R}}_P$ and $\underline{\underline{R}}_E$ for each beam segment before reconstruction.

6. The method of claim 1, wherein said radiation therapy includes use of a megavoltage (MV) x-ray radiation beam.

7. The method of claim 1, wherein said radiation therapy includes use of an on-board imager.

8. A method for verifying radiation therapy in a therapeutic x-ray delivery system for delivering radiation doses in the form of an x-ray beam or x-ray beam segments, said method comprising the steps of:

pretreatment imaging a patient;

planning a radiation dose treatment of said patient through use of a patient image obtained in said pretreatment imaging step;

pretreatment verifying the planned radiation dose to be given to said patient, wherein said pretreatment verifying step includes the steps of:

simulating via calculation the radiation dose derived from a predetermined beam to be emitted from a radiation source on a flat phantom using the results of said planning step;

measuring by positioning said flat phantom at the same position where said calculation was performed and measuring the radiation dose;

comparing the calculated radiation dose from said simulating step with the actual radiation dose obtained from said measurement step; and proceeding to a treating step only if the calculated and actual radiation doses compare to one another within a predetermined accuracy;

treating said patient with said planned radiation dose from the radiation source of said x-ray delivery system;

detecting the transmitted radiation dose image in an electronic portal imaging device (EPID) after passage through said patient;

treatment imaging said patient to obtain anatomical information of said patient under treatment conditions; and inversely verifying the actual radiation dose delivered to said patient through use of both the dose image from said detecting step, and the anatomical information from said treatment imaging step, to determine whether the verified actual radiation dose matches the planned radiation dose, or was either an overdose or underdose compared to the latter, wherein said step of inversely verifying includes the step of solving the following equation:

$$\underline{P}=\underline{\underline{R}}_P\underline{\underline{R}}_E^{-1}\underline{E}$$

where $\underline{P}$ is the vector of P, P is the dose in a phantom, $\underline{\underline{R}}_P$ is the matrix of $R_P$ (beam-to-phantom Response), $\underline{\underline{R}}_E^{-1}$ is the inverse matrix of $R_E$ (beam-to-EPID Response), $\underline{E}$ is the vector of E, and E is the measured dose in EPID.

9. The method of claim 8, wherein said pretreatment imaging step further includes using computer tomography to obtain the pretreatment image of said patient.

10. The method of claim 8, wherein said step of treating includes use of a megavoltage (MV) x-ray radiation source.

11. The method of claim 8, wherein said step of planning further includes the steps of:
determining a total cumulative radiation dose distribution over a period of time via a plurality of spaced apart radiation dose treatments; and
adaptively changing each radiation dose treatment through use of each immediately previous treating step to account for errors determined from the associated inversely verifying step to attain the desired total cumulative radiation dose distribution.

12. The method of claim 8, further including the steps of:
adaptively planning and administering an additional dose of radiation to said patient at a future time, based upon the results of said step of inversely verifying, said step of adaptively planning including the steps of:
decreasing the next planned radiation dose, in the event of an overdose from the last treating step, by an amount equivalent to the amount of the overdose; or
increasing the next planned radiation dose, in the event of an underdose from the last said treating step, by an amount equivalent to the amount of underdose; or
maintaining the next planned radiation dose as planned in the event the verified last radiation dose matched the last planned dose; or
repeating said step of pretreatment verifying for the next planned radiation dose if intensity modulated radiation therapy (IMRT) is to be used in the following treating step, otherwise proceed directly to said treating step;

repeating said treating step with the next planned radiation dose;
repeating said detecting step;
repeating said inversely verifying step; and
repeating said step of adaptively planning and administrating until a planned total cumulative radiation dose distribution has been attained.

13. The method of claim 8, further including the steps of:
including in said therapeutic x-ray delivery system a megavolt x-ray radiation source for use in said step of treating; and
including in said therapeutic x-ray delivery system a kilovolt x-ray source and a kilovolt x-ray detector for use in said step of treatment imaging.

14. The method of claim 8, wherein said inversely verifying step, and said inversely calculating step each further include the step of solving the following equation:

$$\Delta\underline{P}=\underline{\underline{R}}_P\underline{\underline{R}}_E^{-1}\Delta\underline{E}$$

where $\Delta\underline{P}$ is the vector for the difference between planned (forwardly calculated using planned S) and reconstructed doses in a phantom or patient, $\underline{\underline{R}}_P$ is the matrix of $R_P$ (beam-to-phantom Response), $\underline{\underline{R}}_E^{-1}$ is the inverse matrix of $R_E$ (beam-to-EPID Response), and $\Delta\underline{E}=(\underline{E}^{predicted}-\underline{E}^{measured})$ where $\underline{E}^{predicted}$ is the vector for forwardly calculated dose in EPID and $\underline{E}^{measured}$ is the vector for measured dose in EPID.

15. The method of claim 8, wherein said inversely verifying step further includes the step of solving the following equation:

$$\underline{S}=\underline{\underline{R}}_E^{-1}\underline{E}$$

where $\underline{S}$ is the vector of S, a beam intensity map, $\underline{\underline{R}}_E^{-1}$ is the inverse matrix of $R_E$ (beam-to-EPID Response), $\underline{E}$ is the vector of E, is the measured dose in EPID.

16. The method of claim 8, wherein said inversely verifying step further includes the step of solving the following equation:

$$\Delta\underline{S}=\underline{\underline{R}}_E^{-1}\Delta\underline{E},$$

where $\Delta\underline{S}$ is the difference between the imposed and reconstructed intensity, $\underline{\underline{R}}_E^{-1}$ is the inverse matrix of $R_E$ (beam-to-EPID Response), and $\Delta\underline{E}=(\underline{E}^{predicted}-\underline{E}^{measured})$, where $\underline{E}^{predicted}$ is the vector for forwardly calculated dose in EPID and $\underline{E}^{measured}$ is the vector for measured dose in EPID.

17. The method of claim 8, wherein said inversely verifying step further includes the step of acquiring $\underline{\underline{R}}_P$ and $\underline{\underline{R}}_E$ for each beam segment before reconstruction.

18. The method of claim 8, wherein said radiation therapy includes use of a megavoltage (MV) x-ray radiation beam.

19. The method of claim 8, wherein said radiation therapy includes use of an on-board imager.

20. The method of claim 8, wherein said step of planning further includes the steps of:
determining a total cumulative radiation dose distribution over a period of time via a plurality of spaced apart radiation dose treatments; and
adaptively changing each radiation dose treatment through use of each immediately previous treating step to account for errors determined from the associated inversely verifying step to attain the desired total cumulative radiation dose distribution.

* * * * *